United States Patent
Fushimi et al.

(10) Patent No.: US 7,294,618 B2
(45) Date of Patent: Nov. 13, 2007

(54) GLUCOPYRANOSYLOXYPYRAZOLE DERIVATIVES AND MEDICINAL USE THEREOF

(75) Inventors: Nobuhiko Fushimi, Matsumoto (JP); Hideki Fujikura, Matsumoto (JP); Toshihiro Nishimura, Hotaka-machi (JP); Kenji Katsuno, Tatusno-machi (JP); Masayuki Isaji, Shiojiri (JP)

(73) Assignee: Kissei Pharmaceutical Co., Ltd., Nagano (JP)

( * ) Notice: Subject to any disclaimer, the term of this patent is extended or adjusted under 35 U.S.C. 154(b) by 166 days.

(21) Appl. No.: 10/469,140

(22) PCT Filed: Feb. 26, 2002

(86) PCT No.: PCT/JP02/01708

§ 371 (c)(1),
(2), (4) Date: Jan. 12, 2004

(87) PCT Pub. No.: WO02/068440

PCT Pub. Date: Sep. 6, 2002

(65) Prior Publication Data

US 2004/0116357 A1 Jun. 17, 2004

(30) Foreign Application Priority Data

Feb. 27, 2001 (JP) ............................. 2001-053085

(51) Int. Cl.
- A01N 43/04 (2006.01)
- A61K 31/70 (2006.01)
- C07H 17/00 (2006.01)

(52) U.S. Cl. .................. 514/25; 514/35; 514/866; 536/4.1; 536/18.1

(58) Field of Classification Search .............. 514/25, 514/35, 866; 536/4.1, 18.1
See application file for complete search history.

(56) References Cited

U.S. PATENT DOCUMENTS

| | | | |
|---|---|---|---|
| 5,264,451 A | 11/1993 | Kees | |
| 5,274,111 A | 12/1993 | Kees | |
| 5,424,406 A | 6/1995 | Tujihara et al. | |
| 5,731,292 A | 3/1998 | Tujihara et al. | |
| 6,815,428 B2* | 11/2004 | Ohsumi et al. | 514/25 |
| 6,972,283 B2 | 12/2005 | Fujikura et al. | |
| 7,015,201 B2* | 3/2006 | Ohsumi et al. | 514/25 |
| 2006/0128635 A1* | 6/2006 | Fujikura et al. | 514/23 |

FOREIGN PATENT DOCUMENTS

| EP | 0449699 A2 | 10/1991 |
|---|---|---|
| EP | 0598359 A1 | 5/1994 |
| JP | 55-157504 | 12/1980 |
| JP | 4-234851 | 8/1992 |
| WO | WO 01/16147 A1 | 8/2001 |
| WO | WO 02/36602 A1 | 5/2002 |
| WO | WO 02/053573 A1 | 7/2002 |
| WO | WO 02/068439 A1 | 9/2002 |

OTHER PUBLICATIONS

Kenneth L. Kees, et al.; New Patent Antihyperglycamic Agents in db/db Mice; Synthesis and Structure-Activity Relationship Studies of (4-Substituted benzyl)(trifluoromethyl)pyrazoles and -pyrazolones; J. Med. Chem. 1996, 39, 3920-3928.

* cited by examiner

Primary Examiner—Shaojia Anna Jiang
Assistant Examiner—Traviss McIntosh
(74) Attorney, Agent, or Firm—Sughrue Mion Pllc.

(57) ABSTRACT

The present invention provides glucopyranosyloxypyrazole derivatives represented by the general formula:

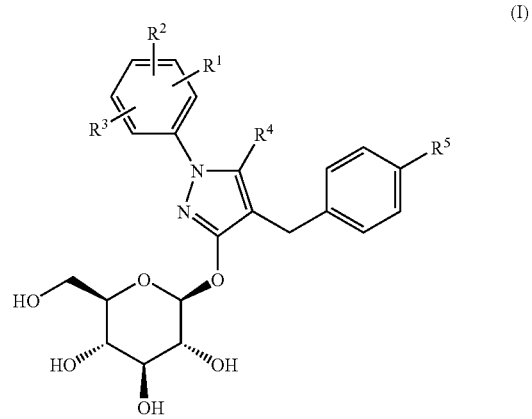

wherein $R^1$, $R^2$ and $R^3$ represent a hydrogen atom or a halogen atom; $R^4$ represents a lower alkyl group or a halo(lower alkyl) group; and $R^5$ represents a hydrogen atom, a lower alkyl group, a lower alkoxy group, a lower alkylthio group, etc., a pharmaceutically acceptable salt thereof or a prodrug thereof., which exert an excellent inhibitory activity in human SGLT2, and therefore are useful as drugs for the prevention or treatment of a disease associated with hyperglycemia such as diabetes, diabetic complications or obesity, pharmaceutically acceptable salts thereof or prodrugs thereof, production intermediates thereof and pharmaceutical uses thereof.

13 Claims, No Drawings

SEQUENCE LISTING

```
<160> NUMBER OF SEQ ID NOS: 5

<210> SEQ ID NO 1
<211> LENGTH: 20
<212> TYPE: DNA
<213> ORGANISM: Artificial Sequence
<220> FEATURE:
<223> OTHER INFORMATION: Synthetic DNA primer

<400> SEQUENCE: 1
atggaggagc acacagaggc                                               20

<210> SEQ ID NO 2
<211> LENGTH: 20
<212> TYPE: DNA
<213> ORGANISM: Artificial Sequence
<220> FEATURE:
<223> OTHER INFORMATION: Synthetic DNA primer

<400> SEQUENCE: 2
ggcatagaag ccccagagga                                               20

<210> SEQ ID NO 3
<211> LENGTH: 29
<212> TYPE: DNA
<213> ORGANISM: Artificial Sequence
<220> FEATURE:
<223> OTHER INFORMATION: Synthetic DNA primer

<400> SEQUENCE: 3
aacctcgaga tggaggagca cacagaggc                                     29

<210> SEQ ID NO 4
<211> LENGTH: 29
<212> TYPE: DNA
<213> ORGANISM: Artificial Sequence
<220> FEATURE:
<223> OTHER INFORMATION: Synthetic DNA primer

<400> SEQUENCE: 4
aacaagcttg gcatagaagc cccagagga                                     29

<210> SEQ ID NO 5
<211> LENGTH: 25
<212> TYPE: PRT
<213> ORGANISM: Artificial Sequence
<220> FEATURE:
<223> OTHER INFORMATION: Peptide fused to the carboxyl terminal
                         alanine residue of human SGLT2

<400> SEQUENCE: 5

Lys Leu Gly Pro Glu Gln Lys Leu Ile Ser Glu Glu Asp Leu Asn Ser
 1               5                  10                  15

Ala Val Asp His His His His His His
            20                  25
```

GLUCOPYRANOSYLOXYPYRAZOLE DERIVATIVES AND MEDICINAL USE THEREOF

TECHNICAL FIELD

The present invention relates to glucopyopyranosyloxypyrazole derivatives, pharmaceutically acceptable salts thereof or prodrugs thereof which are useful as medicaments, production intermediates thereof and pharmaceutical uses thereof.

More particularly, the present invention relates to glucopyranosyloxypyrazole derivatives which have an inhibitory activity in human SGLT2, represented by the general formula:

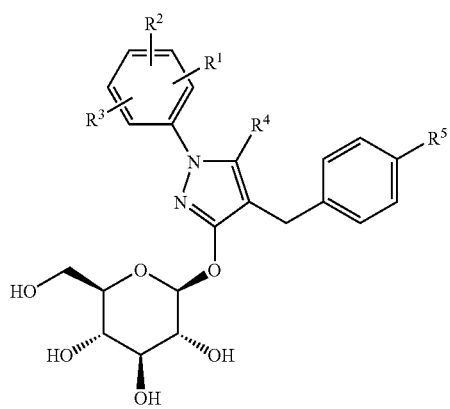

(I)

wherein $R^1$, $R^2$ and $R^3$ may be the same or different and each represents a hydrogen atom or a halogen atom; $R^4$ represents a lower alkyl group or a halo (lower alkyl) group; and $R^5$ represents a hydrogen atom, a lower alkyl group, a lower alkoxy group, a lower alkylthio group, a halo(lower alkyl) group, a halogen atom, a lower alkenyl group, a cyclic lower alkyl group, a cyclic lower alkoxy group, a cyclic lower alkylidenemethyl group, a 5- or 6-membered aromatic heterocyclic group which contains 1-4 the same or different hetero atoms selected from an oxygen atom, a sulfur atom and a nitrogen atom in the ring, a phenyl group which may have 1-3 the same or different groups selected from a halogen atom and a hydroxy group, or a group represented by the general formula: HO-A- wherein A represents a lower alkylene group, pharmaceutically acceptable salts thereof or prodrugs thereof, which are useful as agents for the prevention or treatment of a disease such as diabetes, diabetic complications or obesity, production intermediates thereof and pharmaceutical uses thereof.

BACKGROUND ART

Diabetes is one of lifestyle-related diseases with the background of change of eating habit and lack of exercise. Hence, diet and exercise therapies are performed in patients with diabetes. Furthermore, when its sufficient control and continuous performance are difficult, drug treatment is simultaneously performed. Now, biguanides, sulfonylureas and insulin sensitivity enhancers have been employed as antidiabetic agents. However, biguanides and sulfonylureas show occasionally adverse effects such as lactic acidosis and hypoglycemia, respectively. In a case of using insulin sensitivity enhancers, adverse effects such as edema are occasionally observed, and it is also concerned for advancing obesity. Therefore, in order to solve these problems, it has been desired to develop antidiabetic agents having a new mechanism.

In recent years, development of new type antidiabetic agents has been progressing, which promote urinary glucose excretion and lower blood glucose level by preventing excess glucose reabsorption at the kidney (J. Clin. Invest., Vol. 79, pp. 1510-1515 (1987)). In addition, it is reported that SGLT2 (Na+/glucose cotransporter 2) is present in the S1 segment of the kidney's proximal tubule and participates mainly in reabsorption of glucose filtrated through glomerular (J. Clin. Invest., Vol. 93, pp. 397-404 (1994)). Accordingly, inhibiting a human SGLT2 activity prevents reabsorption of excess glucose at the kidney, subsequently promotes excreting excess glucose though the urine, and normalizes blood glucose level. Therefore, fast development of antidiabetic agents, which have a potent inhibitory activity in human SGLT2 and have a new mechanism, has been desired. In addition, since such agents promote the excretion of excess glucose though the urine and consequently the glucose accumulation in the body is decreased, they are also expected to have a preventing or alleviating effect on obesity and a urinating effect. Furthermore, the agents are considered to be useful for various related diseases which occur accompanying the progress of diabetes or obesity due to hyperglycemia.

As compounds having pyrazole moiety, it is described that WAY-123783 increased an amount of excreted glucose in normal mice. However, its effects in human are not described at all (J. Med. Chem., Vol. 39, pp. 3920-3928 (1996)).

DISCLOSURE OF THE INVENTION

The present inventors have studied earnestly to find compounds having an inhibitory activity in human SGLT2. As a result, it was found that compounds represented by the above general formula (I) show an excellent inhibitory activity in human SGLT2, thereby forming the basis of the present invention.

The present invention is to provide the following glucopyranosyloxypyrazole derivatives, pharmaceutically acceptable salts thereof and prodrugs thereof which exert an inhibitory activity in human SGLT2 and show an excellent hypoglycemic effect by excreting excess glucose in the urine through preventing the reabsorption of glucose at the kidney, production intermediates thereof and pharmaceutical uses thereof.

This is, the present invention relates to a glucopyranosyloxypyrazole derivative represented by the general formula:

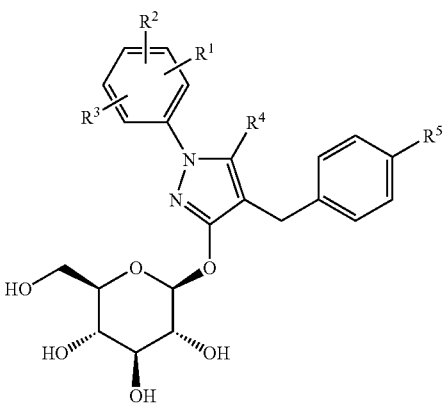

(I)

wherein $R^1$, $R^2$ and $R^3$ may be the same or different and each represents a hydrogen atom or a halogen atom; $R^4$ represents a lower alkyl group or a halo (lower alkyl) group; and $R^5$ represents a hydrogen atom, a lower alkyl group, a lower alkoxy group, a lower alkylthio group, a halo (lower alkyl) group, a halogen atom, a lower alkenyl group, a cyclic lower alkyl group, a cyclic lower alkoxy group, a cyclic lower alkylidenemethyl group, a 5- or 6-membered aromatic heterocyclic group which contains 1-4 the same or different hetero atoms selected from an oxygen atom, a sulfur atom and a nitrogen atom in the ring, a phenyl group which may have 1-3 the same or different groups selected from a halogen atom and a hydroxy group, or a group represented by the general formula: HO-A- wherein A represents a lower alkylene group, a pharmaceutically acceptable salt thereof or a prodrug thereof.

Also, the present invention relates to a pharmaceutical composition, a human SGLT2 inhibitor and an agent for the prevention or treatment of a disease associated with hyperglycemia, which comprise as an active ingredient a glucopyranosyloxypyrazole derivative represented by the above general formula (I), a pharmaceutically acceptable salt thereof or a prodrug thereof.

The present invention relates to a method for the prevention or treatment of a disease associated with hyperglycemia, which comprises administering an effective amount of a glucopyranosyloxypyrazole derivative represented by the above general formula (I), a pharmaceutically acceptable salt thereof or a prodrug thereof.

The present invention relates to a use of a glucopyranosyloxypyrazole derivative represented by the above general formula (I), a pharmaceutically acceptable salt thereof or a prodrug thereof for the manufacture of a pharmaceutical composition for the prevention or treatment of a disease associated with hyperglycemia.

The present invention relates to a pharmaceutical combination which comprises (A) a glucopyranosyloxypyrazole derivative represented by the above general formula (I), a pharmaceutically acceptable salt thereof or a prodrug thereof, and (B) at least one member selected from the group consisting of an insulin sensitivity enhancer, a glucose absorption inhibitor, a biguanide, an insulin secretion enhancer, an insulin preparation, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist, an aldose reductase inhibitor, an advanced glycation endproducts formation inhibitor, a protein kinase C inhibitor, a γ-aminobutyric acid receptor antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor, a platelet-derived growth factor analogue, epidermal growth factor, nerve growth factor, a carnitine derivative, uridine, 5-hydroxy-1-methylhidantoin, EGAB-761, bimoclomol, sulodexide, Y-128, a hydroxymethyl-glutaryl coenzyme A reductase inhibitor, a fibric acid derivative, a $\beta_3$-adrenoceptor agonist, an acyl-coenzyme A cholesterol acyltransferase inhibitor, probcol, a thyroid hormone receptor agonist, a cholesterol absorption inhibitor, a lipase inhibitor, a microsomal triglyceride transfer protein inhibitor, a lipoxygenase inhibitor, a carnitine palmitoyl-transferase inhibitor, a squalene synthase inhibitor, a low-density lipoprotein receptor enhancer, a nicotinic acid derivative, a bile acid sequestrant, a sodium/bile acid cotransporter inhibitor, a cholesterol ester transfer protein inhibitor, an appetite suppressant, an angiotensin-converting enzyme inhibitor, a neutral endopeptidase inhibitor, an angiotensin II receptor antagonist, an endothelin-converting enzyme inhibitor, an endothelin receptor antagonist, a diuretic agent, a calcium antagonist, a vasodilating antihypertensive agent, a sympathetic blocking agent, a centrally acting antihypertensive agent, an $\beta_2$-adrenoceptor agonist, an antiplatelets agent, a uric acid synthesis inhibitor, a uricosuric agent and a urinary alkalinizer.

The present invention relates to a method for the prevention or treatment of a disease associated with hyperglycemia, which comprises administering an effective amount of (A) a glucopyranosyloxypyrazole derivative represented by the above general formula (I), a pharmaceutically acceptable salt thereof or a prodrug thereof, in combination with (B) at least one member selected from the group consisting of an insulin sensitivity enhancer, a glucose absorption inhibitor, a biguanide, an insulin secretion enhancer, an insulin preparation, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist, an aldose reductase inhibitor, an advanced glycation endproducts formation inhibitor, a protein kinase C inhibitor, a γ-aminobutyric acid receptor antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor, a platelet-derived growth factor analogue, epidermal growth factor, nerve growth factor, a carnitine derivative, uridine, 5-hydroxy-1-methylhidantoin, EGB-761, bimoclomol, sulodexide, Y-128, a hydroxymethyl-glutaryl coenzyme A reductase inhibitor, a fibric acid derivative, a $\beta_3$-adrenoceptor agonist, an acyl-coenzyme A cholesterol acyltransferase inhibitor, probcol, a thyroid hormone receptor agonist, a cholesterol absorption inhibitor, a lipase inhibitor, a microsomal triglyceride transfer protein inhibitor, a lipoxygenase inhibitor, a carnitine palmitoyl-transferase inhibitor, a squalene synthase inhibitor, a low-density lipoprotein receptor enhancer, a nicotinic acid derivative, a bile acid sequestrant, a sodium/bile acid cotransporter inhibitor, a cholesterol ester transfer protein inhibitor, an appetite suppressant, an angiotensin-converting enzyme inhibitor, a neutral endopeptidase inhibitor, an angiotensin II receptor antagonist, an endothelin-converting enzyme inhibitor, an endothelin receptor antagonist, a diuretic agent, a calcium antagonist, a vasodilating antihypertensive agent, a sympathetic blocking agent, a centrally acting antihypertensive agent, an $\alpha_2$-adrenoceptor agonist, an antiplatelets agent, a uric acid synthesis inhibitor, a uricosuric agent and a urinary alkalinizer.

The present invention relates to a use of (A) a glucopyranosyloxypyrazole derivative represented by the above general formula (I), a pharmaceutically acceptable salt thereof or a prodrug thereof, and (B) at least one member selected from the group consisting of an insulin sensitivity enhancer, a glucose absorption inhibitor, a biguanide, an insulin secretion enhancer, an insulin preparation, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist, an aldose reductase inhibitor, an advanced glycation endproducts formation inhibitor, a protein kinase C inhibitor, a γ-aminobutyric acid receptor antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor, a platelet-derived growth factor analogue, epidermal growth factor, nerve growth factor, a carnitine derivative, uridine, 5-hydroxy-1-methylhidantoin, EGB-761, bimoclomol, sulodexide, Y-128, a hydroxymethyl-glutaryl coenzyme A reductase inhibitor, a fibric acid derivative, a $\beta_3$-adrenoceptor agonist, an acyl-coenzyme A cholesterol acyltransferase inhibitor, probcol, a thyroid hormone receptor agonist, a cholesterol absorption inhibitor, a lipase inhibitor, a microsomal triglyceride transfer protein inhibitor, a lipoxygenase inhibitor, a carnitine palmitoyl-transferase inhibitor, a squalene synthase inhibitor, a low-density lipoprotein receptor enhancer, a nicotinic acid derivative, a bile acid sequestrant, a sodium/bile acid cotransporter inhibitor, a cholesterol ester transfer protein inhibitor, an appetite suppressant, an angiotensin-converting enzyme inhibitor, a neutral endopeptidase inhibitor, an angiotensin II receptor antagonist, an endothelin-converting enzyme inhibitor, an endothelin receptor antagonist, a diuretic agent, a calcium antagonist, a vasodilating antihypertensive agent, a sympathetic blocking agent, a centrally acting antihypertensive agent, an $\alpha_2$-adrenoceptor agonist, an antiplatelets agent, a uric acid synthesis inhibitor, a uricosuric agent and a urinary alkalinizer, for the manufacture of a pharmaceutical composition for the prevention or treatment of a disease associated with hyperglycemia.

Furthermore, the present invention relates to a glucopyranosyloxypyrazole derivative represented by the general formula:

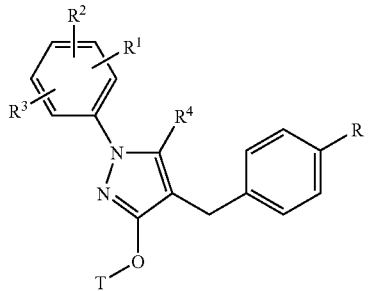

(III)

wherein T represents 2,3,4,6-tetra-O-acetyl-β-D-glucopyranosyl group; $R^1$, $R^2$ and $R^3$ may be the same or different and each represents a hydrogen atom or a halogen atom; $R^4$ represents a lower alkyl group or a halo(lower alkyl) group; and R represents a hydrogen atom, a lower alkyl group, a lower alikoxy group, a lower alkylthio group, a halo(lower alkyl) group, a halogen atom, a lower alkenyl group, a cyclic lower alkyl group, a cyclic lower alkoxy group, a cyclic lower alkylidenemethyl group, a 5- or 6-membered aromatic hetero cyclic group which contains 1-4 the same or different hetero atoms selected from an oxygen atom, a sulfur atom and a nitrogen atom in the ring, a phenyl group which may have 1-3 the same or different groups selected from a halogen atom and a hydroxy group, or a group represented by the general formula: $P^{10}$-O-A- wherein $P^{10}$ represents a hydrogen atom or a hydroxy-protective group; and A represents a lower alkylene group, or a salt thereof, and a benzylpyrazole derivative represented by the general formula:

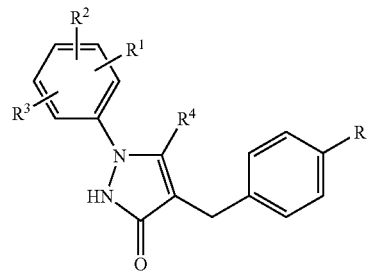

(IV)

wherein $R^1$, $R^2$ and $R^3$ may be the same or different and each represents a hydrogen atom or a halogen atom; $R^4$ represents a lower alkyl group or a halo(lower alkyl) group; and R represents a hydrogen atom, a lower alkyl group, a lower alkoxy group, a lower alkylthio group, a halo(lower alkyl) group, a halogen atom, a lower alkenyl group, a cyclic lower alkyl group, a cyclic lower alkoxy group, a cyclic lower alkylidenemethyl group, a 5- or 6-membered aromatic heterocyclic group which contains 1-4 the same or different hetero atoms selected from an oxygen atom, a sulfur atom and a nitrogen atom in the ring, a phenyl group which may have 1-3 the same or different groups selected from a halogen atom and a hydroxy group, or a group represented by the general formula: $P^{10}$-O-A- wherein $P^{10}$ represents a hydrogen atom or a hydroxy-protective group; and A represents a lower alkylene group, or a salt thereof.

As prodrugs of the above mentioned glucopyranosyloxypyrazole derivatives, a compound represented by the general formula:

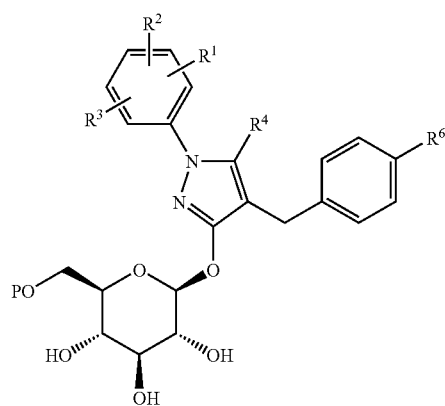

(II)

wherein P represents a hydrogen atom or a group forming a prodrug; $R^1$, $R^2$ and $R^3$ may be the same or different and each represents a hydrogen atom or a halogen atom; $R^4$ represents a lower alkyl group or a halo(lower alkyl) group; $R^6$ represents a hydrogen atom, a lower alkyl group, a lower alkoxy group, a lower alkylthio group, a halo(lower alkyl) group, a halogen atom, a lower alkenyl group, a cyclic lower alkyl group, a cyclic lower alkoxy group, a cyclic lower alkylidenemethyl group, a 5- or 6-membered aromatic heterocyclic group which contains 1-4 the same or different hetero atoms selected from an oxygen atom, a sulfur atom and a nitrogen atom in the ring, a phenyl group which may have 1-3 the same or different groups selected from a halogen atom and a hydroxy group, or a group represented by the general formula: $P^1$-O-A- wherein $p^1$ represents a hydrogen atom or a group forming a prodrug; and A represents a lower alkylene group; and with the proviso that at least one of P and $R^6$ has a group forming a prodrug can be illustrated.

In the present invention, the term "prodrug" means a compound which is converted into a glucopyranosyloxypyrazole derivative represented by the above general formula (I) as an active form thereof in vivo. As examples of groups forming prodrugs, a hydroxy-protective group used generally in a prodrug such as a lower acyl group, a lower alkoxy-substituted (lower acyl) group, a lower alkoxycarbonyl-substituted (lower acyl) group, a lower alkoxycarbonyl group and a lower alkoxy-substituted (lower alkoxycarbonyl) group can be illustrated.

In the present invention, the term "lower alkyl group" means a straight-chained or branched alkyl group having 1 to 6 carbon atoms such as a methyl group, an ethyl group, a propyl group, an isopropyl group, a butyl group, an isobutyl group, a sec-butyl group, a tert-butyl group, a pentyl group, an isopentyl group, a neopentyl group, a tert-pentyl group, a hexyl group or the like; the term "lower alkoxy group" means a straight-chained or branched alkoxy group having 1 to 6 carbon atoms such as a methoxy group, an ethoxy group, a propoxy group, an isopropoxy group, a butoxy group, an isobutoxy group, a sec-butoxy group, a tert-butoxy group, a pentyloxy group, an isopentyloxy group, a neopentyloxy group, a tert-pentyloxy group, a hexyloxy group or the like; and the term "lower alkylthio group" means a straight-chained or branched alkylthio group having 1 to 6 carbon atoms such as a methylthio group, an ethylthio group, a propylthio group, an isopropylthio group, a butylthio group, an isobutylthio group, a sec-butylthio group, a tert-butylthio group, a pentylthio group, an isopentylthio group, a neopentylthio group, a tert-pentylthio group, a hexylthio group or the like. The term "lower alkylene group" means a straight-chained or branched alkylene group having 1 to 6 carbon atoms such as a methylene group, an ethylene group, a trimethylene group, a propylene group or the like; the term "lower alkenyl group" means a straight-chained or branched alkenyl group having 3 to 6 carbon atoms such as an allyl group, a 2-butenyl group, a 2-methylallyl group or the like; the term "cyclic lower alkyl group" means a 3- to 7-membered cyclic alkyl group such as a cyclopropyl group, a cyclobutyl group, a cyclopentyl group, a cyclohexyl group, a cycloheptyl group or the like; the term "cyclic lower alkoxy group" means a 3- to 7-membered cyclic alkoxy group such as a cyclopropyloxy group, a cyclobutyloxy group, a cyclopentyloxy group, a cyclohexyloxy group, a cycloheptyloxy group or the like; and the term "cyclic lower alkylidenemethyl group" means a 3- to 6-membered cyclic alkylidenemethyl group such as a cyclopropylidenemethyl group, a cyclobutylidenemethyl group, a cyclopentylidenemethyl group, a cyclohexylidenemethyl group or the like. The term "halogen atom" means a fluorine atom, a chlorine atom, a bromine atom or an iodine atom; and the term "halo(lower alkyl) group" means the above lower alkyl group substituted by 1 to 3 the same or different halogen atoms defined above. The term "lower acyl group" means a straight-chained, branched or cyclic acyl group having 2 to 7 carbon atoms such as an acetyl group, a propionyl group, a butyryl group, an isobutyryl group, a pivaloyl group, a hexanoyl group, a cyclohexylcarbonyl group or the like; and the term "lower alkoxy-substituted (lower acyl) group means the above lower acyl group substituted by the above lower alkoxy group. The term "lower alkoxycarbonyl group" means a straight-chained, branched or cyclic alkoxycarbonyl group having 2 to 7 carbon atoms such as a methoxycarbonyl group, an ethoxycarbonyl group, a propoxycarbonyl group, an isopropoxycarbonyl group, a butoxycarbonyl group, an isobutoxycarbonyl group, a sec-butoxycarbonyl group, a tert-butoxycarbonyl group, a pentyloxycarbonyl group, an isopentyloxycarbonyl group, a neopentyloxycarbonyl group, a tert-pentyloxycarbonyl group, a hexyloxycarbonyl group, a cyclohexyloxycarbonyl group or the like; the term "lower alkoxycarbonyl-substituted (lower acyl) group" means the above lower acyl group substituted by the above lower alkoxycarbonyl group such as a 3-(ethoxycarbonyl)-propionyl group or the like; and the term "lower alkoxy-substituted (loweralkoxycarbonyl) group" means the above lower alkoxycarbonyl group substituted by the above lower alkoxy group such as a 2-methoxyethoxycarbonyl group or the like. The term "5- or 6-membered aromatic heterocyclic group which contains 1 to 4 the same or different hetero atoms selected from an oxygen atom, a sulfur atom and a nitrogen atom in the ring" means a univalent group derived from an aromatic heterocycle such as furan, thiophene, pyrrole, oxazole, isoxazole, thiazole, isothiazole, pyrazole, imidazole, furazan, tetrazole, pyridine, pyridazine, pyrimidine, pyrazine, triazine or the like. The term "hydroxy-protective group" means a hydroxy-protective group used in general organic syntheses such as a benzyl group, a methoxymethyl group, an acetyl group or the like.

The glucopyranosyloxypyrazole derivatives represented by the above general formula (I) of the present invention and prodrugs thereof can be prepared according to the following procedure:

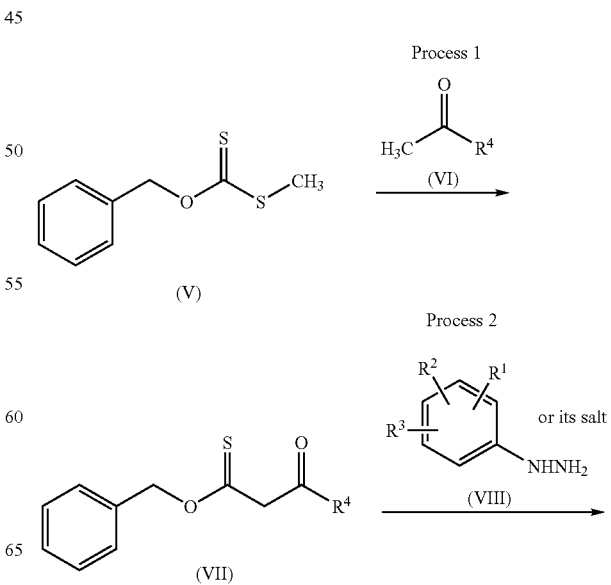

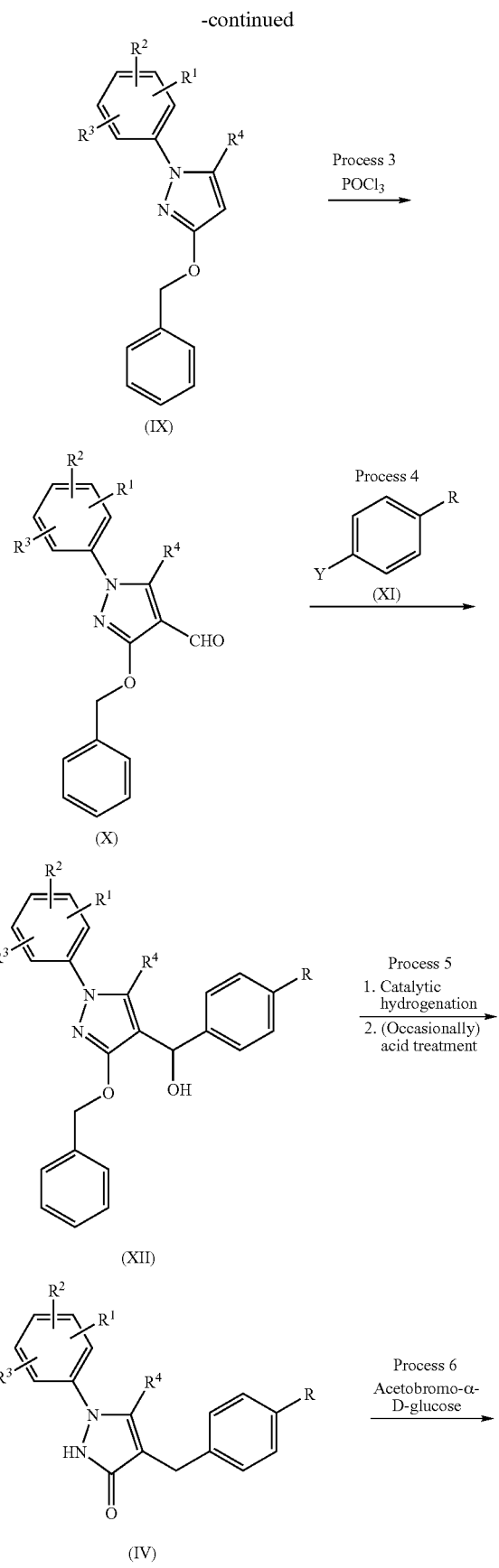

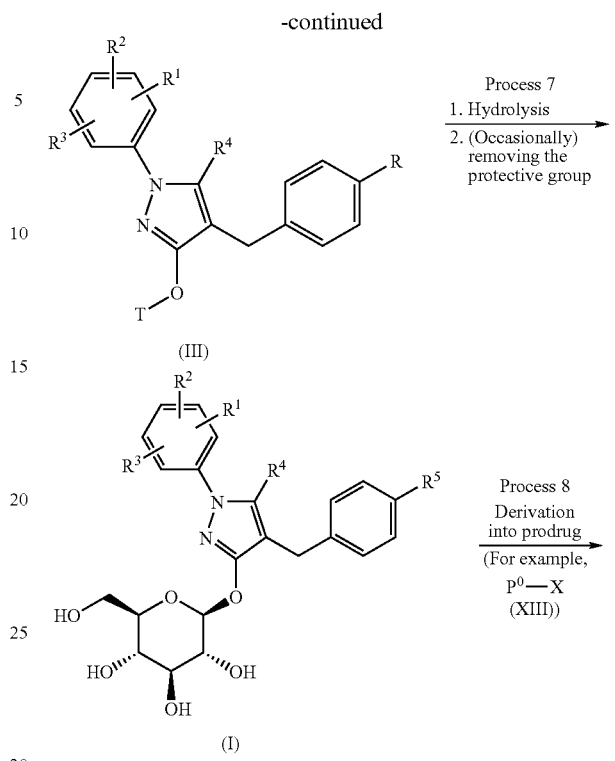

A prodrug of a glucopyranosyl-oxypyrazole derivative represented by the above general formula (I)

wherein $P^0$ represents a group forming a prodrug; X represents a leaving group such as a bromine atom, a chlorine atom or the like; Y represents MgBr, MgCl or a lithium atom; and R, $R^1$, $R^2$, $R^3$, $R^4$, $R^5$ and T have the same meanings as defined above.

Process 1

A compound represented by the above general formula (VII) can be prepared by condensing a dithiocarbonate ester derivative represented by the above general formula (V) with a ketone derivative represented by the above general formula (VI) in the presence of a base such as sodium amide in an inert solvent. As the inert solvent used in the reaction, toluene and the like can be illustrated. The reaction temperature is usually from −20° C. to room temperature, and the reaction time is usually from 30 minutes to 1 day, varying based on a used starting material, solvent and reaction temperature.

Process 2

An N-phenylpyrazole derivative represented by the above general formula (IX) can be prepared by condensing a compound represented by the above general formula (VII) with a phenylhydrazine derivative represented by the above general formula (VIII) or a salt thereof in the presence of a base such as triethylamine, diisopropylethylamine or the like in an inert solvent. As the inert solvent used in the reaction, acetonitrile and the like can be illustrated. The reaction temperature is usually from 0° C. to reflux temperature, and the reaction time is usually from 1 hour to 1 day, varying based on a used starting material, solvent and reaction temperature.

Process 3

A corresponding compound represented by the above general formula (X) can be prepared by subjecting an N-phenylpyrazole derivative to Vilsmeier reaction using phosphorus oxychloride in an inert solvent. As the solvent used in the reaction, N,N-dimethylformamide and the like can be illustrated. The reaction temperature is usually from 0° C. to ref lux temperature, and the reaction time is usually from 30 minutes to 1 day, varying based on a used starting material, solvent and reaction temperature.

Process 4

A compound represented by the above general formula (XII) can be prepared by condensing a compound represented by the above general formula (X) with a Grignard reagent or a lithium reagent represented by the above general formula (XI) in an inert solvent. As the solvent used in the reaction, tetrahydrofuran, diethyl ether, a mixed solvent thereof and the like can be illustrated. The reaction temperature is usually from −78° C. to room temperature, and the reaction time is usually from 30 minutes to 1 day, varying based on a used starting material, solvent and reaction temperature.

Process 5

A benzylpyrazole derivative of the present invention represented by the above general formula (IV) can be prepared by subjecting a compound represented by the above general formula (XII) to catalytic hydrogenation using a palladium catalyst such as palladium-carbon powder in the presence or absence of an acid such as hydrochloric acid in an inert solvent, and for a compound having any sulfur atom represented by the above general formula (XII), subjecting the resulting compound to acid treatment in an aqueous solution of trifluoroacetic acid and dimethyl sulfide usually at 0° C. to reflux temperature for 30 minutes to 1 day as occasion demands. As the solvent used in the catalytic hydrogenation, methanol, ethanol, tetrahydrofuran, ethyl acetate, acetic acid, iropropanol, a mixed solvent thereof and the like can be illustrated. The reaction temperature is usually from room temperature to reflux temperature, and the reaction time is usually from 30 minutes to 1 day, varying based on a used starting material, solvent and reaction temperature. The obtained compound represented by the above general formula (IV) can be also used in Process 6 after converting into a salt thereof in the usual way.

Process 6

A glucopyranosyloxypyrazole derivative of the present invention represented by the above formula (III) can be prepared by subjecting a compound represented by the above general formula (IV) to glucosidation using acetobromo-α-D-glucose in the presence of abase such as sodiumhydroxide, potassium hydroxide, potassium carbonate or the like and a phase transfer catalyst such as benzyltri(n-butyl)ammonium chloride, benzyltri-(n-butyl)ammonium bromide, tetra(n-butyl)ammonium hydrogen sulfate or the like in water and an inert solvent. As the inert solvent used in the glucosidation reaction, dichloromethane, toluene, benzotrifluoride and the like can be illustrated. The reaction temperature is usually from 0° C. to reflux temperature, and the reaction time is usually from 30 minutes to 1 day, varying based on a used starting material, solvent and reaction temperature. The obtained compound represented by the above general. formula (III) can be also used in Process 7 after converting into a salt thereof in the usual way.

In the compounds represented by the above general formula (IV) of the present invention as starting materials, there can be the following two tautomers, varying based on difference in the reaction conditions. The compounds represented by the above general formula (IV) of the present invention include both compounds described as the following states:

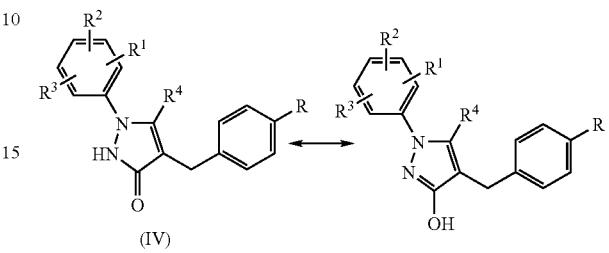

(IV)

Process 7

A glucopyranosyloxypyrazole derivative of the present invention represented by the above general formula (I) can be prepared by subjecting a compound represented by the above general formula (III) to alkaline hydrolysis and optionally removal of a hydroxy-protective group in the usual way. As the solvent used in the hydrolysis reaction, methanol, ethanol, tetrahydrofuran, water, a mixed solvent thereof and the like can be illustrated. As the base, sodium hydroxide, sodium methoxide, sodium ethoxide and the like can be illustrated. The reaction temperature is usually from 0° C. to reflux temperature, and the reaction time is usually from 30 minutes to 1 day, varying based on a used starting material, solvent and reaction temperature.

Process 8

A prodrug of a glucopyranosyloxypyrazole derivative represented by the above general formula (I) including a prodrug represented by the above general formula (II) can be prepared by introducing a hydroxy group generally capable for use in a prodrug into a hydroxy group of a glucopyranosyloxypyrazole derivative represented by the above general formula (I) in the usual way, for example, using a hydroxy-protecting reagent represented by the above general formula (XIII).

The glucopyranosyloxypyrazole derivatives represented by the above general formula (I) of the present invention and the prodrugs thereof obtained by the above production processes can be isolated and purified by conventional separation means such as fractional recrystallization, purification using chromatography, solvent extraction and solid phase extraction.

The glucopyranosyloxypyrazole derivatives represented by the above general formula (I) of the present invention and prodrugs thereof can be converted into their pharmaceutically acceptable salts in the usual way. Examples of such salts include acid addition salts with mineral acids such as hydrochloric acid, hydrobromic acid, hydroiodic acid, sulfuric acid, nitric acid, phosphoric acid and the like, acid addition salts with organic acids such as formic acid, acetic acid, adipic acid, citric acid, fumaric acid, maleic acid, oleic acid, lactic acid, stearic acid, succinic acid, tartaric acid, propionic acid, butyric acid, oxalic acid, malonic acid, malic acid, carbonic acid, glutamic acid, aspartic acid, methanesulfonic acid, benzenesulfonic acid, p-toluenesulfonic acid and the like, salts with organic amines such as 2-aminoethanol, piperidine, morpholine, pyrrolidine and the like, and salts with inorganic bases such as a sodium salt, a potassium salt, a calcium salt, a magnesium salt and the like.

The glucopyranosyloxypyrazole derivatives represented by the above general formula (I) of the present invention and prodrugs thereof include their solvates with pharmaceutically acceptable solvents such as ethanol, water or the like.

Among the glucopyranosyloxypyrazole derivatives represented by the above general formula (I) of the present invention and prodrugs thereof, there are two geometrical isomers in each compound having an unsaturated bond. In the present invention, either of cis(Z)-isomer or trans(E)-isomer can be employed.

Among the glucopyranosyloxypyrazole derivatives represented by the above general formula (I) of the present invention and prodrugs thereof, there are two optical isomers, R-isomer and S-isomer, in each compound having an asymmetric carbon atom excluding the glucopyranosyloxy moiety. In the present invention, either of R-isomer or S-isomer can be employed, and a mixture of both isomers can be also employed.

The glucopyranosyloxypyrazole derivatives represented by the above general formula (I) of the present invention and prodrugs thereof show an excellent inhibitory activity in human SGLT2. On the other hand, since WAY-123783 has an extremely weak inhibitory activity in human SGLT2, it can not be expected that it exerts an enough effect as a human SGLT2 inhibitor. Therefore, the glucopyranosyloxypyrazole derivatives of the present invention and prodrugs thereof are extremely useful as drugs for the prevention or treatment of a disease associated with hyperglycemia such as diabetes, diabetic complications (e.g., retinopathy, neuropathy, nephropathy, ulcer, macroangiopathy), obesity, hyperinsulinemia, glucose metabolism disorder, hyperlipidemia, hypercholesterolemia, hypertriglyceridemia, lipid metabolism disorder, atherosclerosis, hypertension, congestive heart failure, edema, hyperuricemia, gout or the like.

Furthermore, the compounds of the present invention can be suitably used in combination with at least one member selected from drugs other than SGLT2 inhibitors. Examples of the drugs which can be used in combination with the compounds of the present invention include an insulin sensitivity enhancer, a glucose absorption inhibitor, a biguanide, an insulin secretion enhancer, an insulin preparation, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, ahepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist, an aldose reductase inhibitor, an advanced glycation endproducts formation inhibitor, a protein kinase C inhibitor, a γ-aminobutyric acid receptor antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor (PDGF), a platelet-derived growth factor (PDGF) analogue (e.g., PDGF-AA, PDGF-BB, PDGF-AB), epidermal growth factor (EGF), nerve growth factor, a carnitine derivative, uridine, 5-hydroxy-1-methylhidantoin, EGB-761, bimoclomol, sulodexide, Y-128, a hydroxymethyl-glutaryl coenzyme A reductase inhibitor, a fibric acid derivative, a β3-adrenoceptor agonist, an acyl-coenzyme A cholesterol acyltransferase inhibitor, probcol, a thyroid hormone receptor agonist, a cholesterol absorption inhibitor, a lipase inhibitor, a microsomal triglyceride transfer protein inhibitor, a lipoxygenase inhibitor, a carnitine palmitoyltransferase inhibitor, a squalene synthase inhibitor, a low-density lipoprotein receptor enhancer, a nicotinic acid derivative, a bile acid sequestrant, a sodium/bile acid cotransporter inhibitor, a cholesterol ester transfer protein inhibitor, an appetite suppressant, an angiotensin-converting enzyme inhibitor, a neutral endopeptidase inhibitor, an angiotensin II receptor antagonist, an endothelin-converting enzyme inhibitor, an endothelin receptor antagonist, a diuretic agent, a calcium antagonist, a vasodilating antihypertensive agent, a sympathetic blocking agent, a centrally acting antihypertensive agent, an $\alpha_2$-adrenoceptor agonist, an antiplatelets agent, a uric acid synthesis inhibitor, a uricosuric agent and a urinary alkalinizer.

In case of uses of the compound of the present invention in combination with the above one or more drugs, the present invention includes either dosage forms of simultaneous administration as a single preparation or separated preparations in way of the same or different administration route, and administration at different dosage intervals as separated preparations in way of the same or different administration route A pharmaceutical combination comprising the compound of the present invention and the above one or more drugs includes both dosage forms as a single preparation and separated preparations for combination as mentioned above.

The compounds of the present invention can obtain more advantageous effects than additive effects in the prevention or treatment of the above diseases when using suitably in combination with the above drugs. Also, the administration dose can be decreased in comparison with administration of either drug alone, or adverse effects of coadministered drugs other than SGLT2 inhibitors can be avoided or declined.

Concrete compounds as the above drugs used for combination and preferable diseases to be treated are exemplified as follows. However, the present invention is not limited thereto, and for example, the concrete compounds include their free compounds, and their or other pharmaceutically acceptable salts.

As insulin sensitivity enhancers, peroxisome proliferator-activated receptor-γ agonists such as troglitazone, pioglitazone hydrochloride, rosiglitazone maleate, sodium darglitazone, GI-262570, isaglitazone, LG-100641, NC-2100, T-174, DRF-2189, CLX-0921, CS-011, GW-1929, ciglitazone, sodium englitazone and NIP-221, peroxisome proliferator-activated receptor-α agonists such as GW-9578 and BM-170744, peroxisome proliferator-activated receptor-α/γ agonists such as GW-409544, KRP-297, NN-622, CLX-0940, LR-90, SB-219994, DRF-4158 and DRF-MDX8, retinoid X receptor agonists such as ALRT-268, AGN-4204, MX-6054, AGN-194204, LG-100754 and bexarotene, and other insulin sensitivity enhancers such as reglixane, ONO-5816, MBX-102, CRE-1625, FK-614, CLX-0901, CRE-1633, NN-2344, BM-13125, BM-501050, HQL-975, CLX-0900, MBX-668, MBX-675, S-15261, GW-544, AZ-242, LY-510929, AR-H049020 and GW-501516 are illustrated. Insulin sensitivity enhancers are used preferably for diabetes, diabetic complications, obesity, hyperinsulinemia, glucose metabolism disorder, hyperlipidemia, hypercholesterolemia, hypertriglyceridemia, lipid metabolism disorder or atherosclerosis, and more preferably for diabetes, hyperinsulinemia or glucose metabolism disorder because of improving the disturbance of insulin signal transduction in peripheral tissues and enhancing glucose uptake into the tissues from the blood, leading to lowering blood glucose level.

As glucose absorption inhibitors, α-glucosidase inhibitors such as acarbose, voglibose, miglitol, CKD-711, emiglitate, MDL-25,637, camiglibose and MDL-73,945, and α-amylase inhibitors such as AZM-127 are illustrated. Glucose absorption inhibitors are used preferably for diabetes, diabetic complications, obesity, hyperinsulinemia or glucose metabolism disorder, and more preferably for diabetes or glucose metabolism disorder because of inhibiting the gastrointestinal enzymatic digestion of carbohydrates contained in foods, and inhibiting or delaying the absorption of glucose into the body.

As biguanides, phenformin, buformin hydrochloride, metformin hydrochloride and the like are illustrated. Biguanides are used preferably for diabetes, diabetic complications, hyperinsulinemia or glucose metabolism disorder, and more preferably for diabetes, hyperinsulinemia or glucose metabolism disorder because of lowering blood glucose level by inhibitory effects on hepatic gluconeogenesis, accelerating effects on anaerobic glycolysis in tissues or improving effects on insulin resistance in peripheral tissues.

As insulin secretion enhancers, tolbutamide, chlorpropamide, tolazamide, acetohexamide, glyclopyramide, glyburide (glibenclamide), gliclazide, 1-butyl-3-metanilylurea, carbutamide, glibornuride, glipizide, gliquidone, glisoxapide, glybuthiazol, glybuzole, glyhexamide, sodium glymidine, glypinamide, phenbutamide, tolcyclamide, glimepiride, nateglinide, mitiglinide calcium hydrate, repaglinide and the like are illustrated. Insulin secretion enhancers are used preferably for diabetes, diabetic complications or glucose metabolism disorder, and more preferably for diabetes or glucose metabolism disorder because of lowering blood glucose level by acting on pancreatic β-cells and enhancing the insulin secretion.

As insulin preparations, human insulin, human insulin analogues, animal-deprived insulin and the like are illustrated. Insulin preparations are used preferably for diabetes, diabetic complications or glucose metabolism disorder, and more preferably for diabetes or glucose metabolism disorder.

As glucagon receptor antagonists, BAY-27-9955, NNC-92-1687 and the like are illustrated; as insulin receptor kinase stimulants, TER-17411, L-783281, KRX-613 and the like are illustrated; as tripeptidyl peptidase II inhibitors, UCL-1397 and the like are illustrated; as dipeptidyl peptidase IV inhibitors, NVP-DPP728A, TSL-225, P-32/98 and the like are illustrated; as protein tyrosine phosphatase 1B inhibitors, PTP-112, OC-86839, PNU-177496 and the like are illustrated; as glycogen phosphorylase inhibitors, NN-4201, CP-368296 and the like are illustrated; as fructose-bisphosphatase inhibitors, R-132917 and the like are illustrated; as pyruvate dehydrogenase inhibitors, AZD-7545 and the like are illustrated; as hepatic gluconeogenesis inhibitors, FR-225659 and the like are illustrated; as glucagon-like peptide-1 analogues, exendin-4, CJC-1131 and the like are illustrated; as glucagon-like peptide 1 agonists; AZM-134, LY-315902 and the like are illustrated; and as amylin, amylin analogues or amylin agonists, pramlintide acetate and the like are illustrated. These drugs, glucose-6-phosphatase inhibitors, D-chiroinsitol, glycogen synthase kinase-3 inhibitors, glucagon-like peptide-1 are used preferably for diabetes, diabetic complications, hyperinsulinemia or glucose metabolism disorder, and more preferably for diabetes or glucose metabolism disorder.

As aldose reductase inhibitors, ascorbyl gamolenate, tolrestat, epalrestat, ADN-138, BAL-ARI8, ZD-5522, ADN-311, GP-1447, IDD-598, fidarestat, sorbinil, ponalrestat, risarestat, zenarestat, minalrestat, methosorbinil, AL-1567, imirestat, M-16209, TAT, AD-5467, zopolrestat, AS-3201, NZ-314, SG-210, JTT-811, lindolrestat and the like are illustrated. Aldose reductase inhibitors are preferably used for diabetic complications because of inhibiting aldose reductase and lowering excessive intracellular accumulation of sorbitol in accelerated polyol pathway which are in continuous hyperglycemic condition in the tissues in diabetic complications.

As advanced glycation endproducts formation inhibitors, pyridoxamine, OPB-9195, ALT-946, ALT-711, pimagedine hydrochloride and the like are illustrated. Advanced glycation endproducts formation inhibitors are preferably used for diabetic complications because of inhibiting formation of advanced glycation endproducts which are accelerated in continuous hyperglycemic condition in diabetes and declining cellular damage.

As protein kinase C inhibitors, LY-333531, midostaurin and the like are illustrated. Protein kinase C inhibitors are preferably used for diabetic complications because of inhibiting protein kinase C activity which is accelerated in continuous hyperglycemic condition in diabetes.

As γ-aminobutyric acid receptor antagonists, topiramate and the like are illustrated; as sodium channel antagonists, mexiletine hydrochloride, oxcarbazepine and the like are illustrated; as transcript factor NF-κB inhibitors, dexlipotam and the like are illustrated; as lipid peroxidase inhibitors, tirilazad mesylate and the like are illustrated; as N-acetylated-α-linked-acid-dipeptidase inhibitors, GPI-5693 and the like are illustrated; and as carnitine derivatives, carnitine, levacecarnine hydrochloride, levocarnitine chloride, levocarnitine, ST-261 and the like are illustrated. These drugs, insulin-like growth factor-I, platelet-derived growth factor, platelet derived growth factor analogues, epidermal growth factor, nerve growth factor, uridine, 5-hydroxy-1-methylhidantoin, EGB-761, bimoclomol, sulodexide and Y-128 are preferably used for diabetic complications.

As hydroxymethylglutaryl coenzyme A reductase inhibitors, sodium cerivastatin, sodium pravastatin, lovastatin, simvastatin, sodium fluvastatin, atorvastatin calcium hydrate, SC-45355, SQ-33600, CP-83101, BB-476, L-669262, S-2468, DMP-565, U-20685, BAY-x-2678, BAY-10-2987, calcium pitavastatin, calcium rosuvastatin, colestolone, dalvastatin, acitemate, mevastatin, crilvastatin, BMS-180431, BMY-21950, glenvastatin, carvastatin, BMY-22089, bervastatin and the like are illustrated. Hydroxymethylglutaryl coenzyme A reductase inhibitors are used preferably for hyperlipidemia, hypercholesterolemia, hypertriglyceridemia, lipid metabolism disorder or atherosclerosis, and more preferably for hyperlipidemia, hypercholesterolemia or atherosclerosis because of lowering blood cholesterol level by inhibiting hydroxymethylglutaryl coenzyme A reductase.

As fibric acid derivatives, bezafibrate, beclobrate, binifibrate, ciprof ibrate, clinofibrate, clofibrate, aluminum clofibrate, clofibric acid, etofibrate, fenofibrate, gemfibrozil, nicofibrate, pirifibrate, ronifibrate, simfibrate, theofibrate, AHL-157 andthelikeare illustrated. Fibric acid derivatives are used preferably for hyperinsulinemia, hyperlipidemia, hypercholesterolemia, hypertriglyceridemia, lipid metabolism disorder or atherosclerosis, and more preferably for hyperlipidemia, hypertriglyceridemia or atherosclerosis because of activating hepatic lipoprotein lipase and enhancing fatty acid oxidation, leading to lowering blood triglyceride level.

As $\beta_3$-adrenoceptor agonists, BRL-28410, SR-58611A, ICI-198157, ZD-2079, BMS-194449, BRL-37344, CP-331679, CP-114271, L-750355, BMS-187413, SR-59062A, BMS-210285, LY-377604, SWR-0342SA, AZ-40140, SB-226552, D-7114, BRL-35135, FR-149175, BRL-26830A, CL-316243, AJ-9677, GW-427353, N-5984, GW-2696 and the like are illustrated. $\beta_3$-Adrenoceptor agonists are used preferably for obesity, hyperinsulinemia, hyperlipidemia, hypercholesterolemia, hypertriglyceridemia or lipid metabolism disorder, and more preferably for obesity or hyperinsulinemia because of stimulating $\beta_3$-adrenoceptor in adipose tissue and enhancing the fatty acid oxidation, leading to induction of energy expenditure.

As acyl-coenzyme A cholesterol acyltransferase inhibitors, NTE-122, MCC-147, PD-132301-2, DUP-129, U-73482, U-76807, RP-70676, P-06139, CP-113818, RP-73163, FR-129169, FY-038, EAB-309, KY-455, LS-3115, FR-145237, T-2591, J-104127, R-755, FCE-28654, YIC-C8-434, avasimibe, CI-976, RP-64477, F-1394, eldacimibe, CS-505, CL-283546, YM-17E, lecimibide, 447C88, YM-750, E-5324, KW-3033, HL-004, eflucimibe and the like are illustrated. Acyl-coenzyme A cholesterol acyltransferase inhibitors are used preferably for hyperlipidemia, hypercholesterolemia, hypertriglyceridemia or lipid metabolism disorder, and more preferably for hyperlipidemia or hypercholesterolemia because of lowering blood cholesterol level by inhibiting acyl-coenzyme A cholesterol acyltransferase.

As thyroid hormone receptor agonists, sodium liothyronine, sodium levothyroxine, KB-2611 and the like are illustrated; as cholesterol absorption inhibitors, ezetimibe, SCH-48461 and the like are illustrated; as lipase inhibitors, or list at, ATL-962, AZM-131, RED-103004 and the like are illustrated; as carnitine palmitoyltransferase inhibitors, etomoxir and the like are illustrated; as squalene synthase inhibitors, SDZ-268-198, BMS-188494, A-87049, RPR-101821, ZD-9720, RPR-107393, ER-27856 and the like are illustrated; as nicotinic acid derivatives, nicotinic acid, nicotinamide, nicomol, niceritrol, acipimox, nicorandil and the like are illustrated; as bile acid sequestrants, colestyramine, colestilan, colesevelam hydrochloride, GT-102-279 and the like are illustrated; as sodium/bile acid cotransporter inhibitors, 264W94, S-8921, SD-5613 and the like are illustrated; and as cholesterol ester transfer protein inhibitors, PNU-107368E, SC-795, JTT-705, CP-529414 and the like are illustrated. These drugs, probcol, microsomal triglyceride transfer protein inhibitors, lipoxygenase inhibitors and low-density lipoprotein receptor enhancers are preferably used for hyperlipidemia, hypercholesterolemia, hypertriglyceridemia or lipidmetabolism disorder.

As appetite suppressants, monoamine reuptake inhibitors, serotonin reuptake inhibitors, serotonin releasing stimulants, serotonin agonists (especially $5HT_{2c}$-agonists), noradrenalin reuptake inhibitors, noradrenalin releasing stimulants, $\alpha_1$-adrenoceptor agonists, $\beta_2$-adrenoceptor agonists, dopamine agonists, cannabinoid receptor antagonists, $\gamma$-aminobutyric acid receptor antagonists, $H_3$-histamine antagonists, L-histidine, leptin, leptin analogues, leptin receptor agonists, melanocortin receptor agonists (especially, MC3-R agonists, MC4-R agonists), $\alpha$-melanocyte stimulating hormone, cocaine-and amphetamine-regulated transcript, mahogany protein, enterostatin agonists, calcitonin, calcitonin-gene-related peptide, bombesin, cholecystokinin agonists (especially CCK-A agonists), corticotropin-releasing hormone, corticotrophin-releasing hormone analogues, corticotropin-releasing hormone agonists, urocortin, somatostatin, somatostatin analogues, somatostatin receptor agonists, pituitary adenylate cyclase-activating peptide, brain-derived neurotrophic factor, ciliary neurotrophic factor, thyrotropin-releasing hormone, neurotensin, sauvagine, neuropeptide Y antagonists, opioid peptide antagonists, galanin antagonists, melanin-concentrating hormone antagonists, agouti-related protein inhibitors and orexin receptor antagonists are illustrated. Concretely, as monoamine reuptake inhibitors, mazindol and the like are illustrated; as serotonin reuptake inhibitors, dexfenfluramine hydrochloride, fenfluramine, sibutramine hydrochloride, fluvoxamine maleate, sertraline hydrochloride and the like are illustrated; as serotonin agonists, inotriptan, (+)-norfenfluramine and the like are illustrated; as noradrenaline reuptake inhibitors, bupropion, GW-320659 and the like are illustrated; as noradrenaline releasing stimulants, rolipram, YM-992 and the like are illustrated; as $\beta_2$-adrenoceptor agonists, amphetamine, dextroamphetamine, phentermine, benzphetamine, methamphetamine, phendimetrazine, phenmetrazine, diethylpropion, phenylpropanolamine, clobenzorex and the like are illustrated; as dopamine agonists, ER-230, doprexin, bromocriptine mesylate and the like are illustrated; as cannabinoid receptor antagonists, rimonabant and the like are illustrated; as $\gamma$-aminobutyric acid receptor antagonists, topiramate and the like are illustrated; as $H_3$-histamine antagonists, GT-2394 and the like are illustrated; as leptin, leptin analogues or leptin receptor agonists, LY-355101 and the like are illustrated; as cholecystokinin agonists (especially CCK-A agonists), SR-146131, SSR-125180, BP-3.200, A-71623; FPL-15849, GI-248573, GW-7178, GI-181771, GW-7854, A-71378 and the like are illustrated; and as neuropeptide Y antagonists, SR-120819-A, PD-160170, NGD-95-1, BIBP-3226, 1229-U-91, CGP-71683, BIBO-3304, CP-671906-01, J-115814 and the like are illustrated. Appetite suppressants are used preferably for diabetes, diabetic complications, obesity, glucose metabolism disorder, hyperlipidemia, hypercholesterolemia, hypertriglyceridemia, lipid metabolism disorder, atherosclerosis, hypertension, congestive heart failure, edema, hyperuricemia or gout, and more preferably for obesity because of stimulating or inhibiting the activities of intracerebral monoamines or bioactive peptides in central appetite regulatory system and suppressing the appetite, leading to reduction of energy intake.

As angiotensin-converting enzyme inhibitors, captopril, enalapri maleate, alacepril, delapril hydrochloride, ramipril, lisinopril, imidaprilhydrochloride, benazepril hydrochloride, ceronapril monohydrate, cilazapril, sodium fosinopril, perindopril erbumine, calcium moveltipril, quinapril hydrochloride, spirapril hydrochloride, temocapril hydrochloride, trandolapril, calcium zofenopril, moexipril hydrochloride, rentiapril and the like are illustrated. Angiotensin-converting enzyme inhibitors are preferably used for diabetic complications or hypertension.

As neutral endopeptidase inhibitors, omapatrilat, MDL-100240, fasidotril, sampatrilat, GW-660511X, mixanpril, SA-7060, E-4030, SLV-306, ecadotril and the like are illustrated. Neutral endopeptidase inhibitors are preferably used for diabetic complications or hypertension.

As angiotensin II receptor antagonists, candesartan cilexetil, candesartan cilexetil/hydrochlorothiazide, potassium losartan, eprosartan mesylate, valsartan, telmisartan, irbesartan, EXP-3174, L-158809, EXP-3312, olmesartan, tasosartan, KT-3-671, GA-0113, RU-64276, EMD-90423, BR-9701 and the like are illustrated. Angiotensin II receptor antagonists are preferably used for diabetic complications or hypertension.

As endothelin-converting enzyme inhibitors, CGS-31447, CGS-35066, SM-19712 and the like are illustrated; as endothelin receptor antagonists, L-749805, TBC-3214, BMS-182874, BQ-610, TA-0201, SB-215355, PD-180988, sodium sitaxsentan, BMS-193884, darusentan, TBC-3711, bosentan, sodium tezosentan, J-104132, YM-598, S-0139, SB-234551, RPR-118031A, ATZ-1993, RO-61-1790, ABT-546, enlasentan, BMS-207940 and the like are illustrated. These drugs are preferably used for diabetic complications or hypertension, and more preferably for hypertension.

As diuretic agents, chlorthalidone, metolazone, cyclopenthiazide, trichloromethiazide, hydrochlorothiazide, hydroflumethiazide, benzylhydrochlorothiazide, penflutizide, methyclothiazide, indapamide, tripamide, mefruside, azosemide, etacrynic acid, torasemide, piretanide, furosemide, bumetanide, meticrane, potassium canrenoate, spironolactone, triamterene, aminophylline, cicletanine hydrochloride, LLU-α, PNU-80873A, isosorbide, D-mannitol, D-sorbitol, fructose, glycerin, acetazolamide, methazolamide, FR-179544, OPC-31260, lixivaptan, conivaptan hydrochloride and the like are illustrated. Diuretic drugs are preferably used for diabetic complications, hypertension, congestive heart failure or edema, and more preferably for hypertension, congestive heart failure or edema because of reducing blood pressure or improving edema by increasing urinary excretion.

As calcium antagonists, aranidipine, efonidipine hydrochloride, nicardipine hydrochloride, barnidipine hydrochloride, benidipine hydrochloride, manidipine hydrochloride, cilnidipine, nisoldipine, nitrendipine, nifedipine, nilvadipine, felodipine, amlodipine besilate, pranidipine, lercanidipine hydrochloride, isradipine, elgodipine, azelnidipine, lacidipine, vatanidipine hydrochloride, lemildipine, diltiazem hydrochloride, clentiazem maleate, verapamil hydrochloride, S-verapamil, fasudil hydrochloride, bepridil hydrochloride, gallopamil hydrochloride and the like are illustrated; as vasodilating antihypertensive agents, indapamide, todralazine hydrochloride, hydralazine hydrochloride, cadralazine, budralazine and the like are illustrated; as sympathetic blocking agents, amosulalol hydrochloride, terazosin hydrochloride, bunazosin hydrochloride, prazosin hydrochloride, doxazosin mesylate, propranolol hydrochloride, atenolol, metoprolol tartrate, carvedilol, nipradilol, celiprolol hydrochloride, nebivolol, betaxolol hydrochloride, pindolol, tertatolol hydrochloride, bevantolol hydrochloride, timolol maleate, carteolol hydrochloride, bisoprolol hemifumarate, bopindolol malonate, nipradilol, penbutolol sulfate, acebutolol hydrochloride, tilisolol hydrochloride, nadolol, urapidil, indoramin and the like are illustrated; as centrally acting antihypertensive agents, reserpine and the like are illustrated; and as α$_2$-adrenoceptor agonists, clonidine hydrochloride, methyldopa, CHF-1035, guanabenz acetate, guanfacine hydrochloride, moxonidine, lofexidine, talipexole hydrochloride and the like are illustrated. These drugs are preferably used for hypertension.

As antiplatelets agents, ticlopidine hydrochloride, dipyridamole, cilostazol, ethyl icosapentate, sarpogrelate hydrochloride, dilazep dihydrochloride, trapidil, beraprost sodium, aspirin and the like are illustrated. Antiplatelets agents are preferably used for atherosclerosis or congestive heart failure.

As uric acid synthesis inhibitors, allopurinol, oxypurinol and the like are illustrated; as uricosuric agents, benzbromarone, probenecid and the like are illustrated; and as urinary alkalinizers, sodium hydrogen carbonate, potassium citrate, sodium citrate and the like are illustrated. These drugs are preferably used for hyperuricemia or gout.

In case of use in combination with drugs other than SGLT2 inhibitors, for example, in the use for diabetes, the combination with at least one member of the group consisting of an insulin sensitivity enhancer, a glucose absorption inhibitor, a biguanide, an insulin secretion enhancer, an insulin preparation, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist and an appetite suppressant is preferable; the combination with at least one member of the group consisting of an insulin sensitivity enhancer, a glucose absorption inhibitor, a biguanide, an insulin secretion enhancer, an insulin preparation, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue and an amylin agonist is more preferable; and the combination with at least one member of the group consisting of an insulin sensitivity enhancer, a glucose absorption inhibitor, a biguanide, an insulin secretion enhancer and an insulin preparation is most preferable. Similarly, in the use for diabetic complications, the combination with at least one member of the group consisting of an insulin sensitivity enhancer, a glucose absorption inhibitor, a biguanide, an insulin secretion enhancer, an insulin preparation, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, glycogen synthase kinase-3 inhibitors, glucagon-likepeptide-1, a glucagon-likepeptide-1 analogue, a glucagon-like peptide-1 agonist, amylin, an amylin analogue, an amylin agonist, an aldose reductase inhibitor, an advanced glycation endproducts formation inhibitor, a protein kinase C inhibitor, a γ-aminobutyric acid antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor, a platelet derived growth factor analogue, epidermal growth factor, nerve growth factor, a carnitine derivative, uridine, 5-hydroxy-1-methylhidantoin, EGB-761, bimoclomol, sulodexide, Y-128, an angiotensin-converting enzyme inhibitor, a neutral endopeptidase inhibitor, an angiotensin II receptor antagonist, an endothelin-converting enzyme inhibitor, an endothelin receptor antagonist and a diuretic agent is preferable; and the combination with at least one member of the group consisting of an aldose reductase inhibitor, an angiotensin-converting enzyme inhibitor, a neutral endopeptidase inhibitor and an angiotensin II receptor antagonist is more preferable. Furthermore, in the use for obesity, the combination with at least one member of the group consisting of an insulin sensitivity enhancer, a glucose absorption inhibitor, a biguanide, an insulin secretion enhancer, an insulin preparation, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, ahepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist, a $\beta_3$-adrenoceptor agonist and an appetite suppressant is preferable; and the combination with at least one member of the group consisting of a $\beta_3$-adrenoceptor agonist and an appetite suppressant is more preferable.

When the pharmaceutical compositions of the present invention are employed in the practical treatment, various dosage forms are used depending on their uses. As examples of the dosage forms, powders, granules, fine granules, dry syrups, tablets, capsules, injections, solutions, ointments, suppositories, poultices and the like are illustrated, which are orally or parenterally administered.

These pharmaceutical compositions can be prepared by admixing with or by diluting and dissolving an appropriate pharmaceutical additive such as excipients, disintegrators, binders, lubricants, diluents, buffers, isotonicities, antiseptics, moistening agents, emulsifiers, dispersing agents, stabilizing agents, dissolving aids and the like, and formulating the mixture in accordance with pharmaceutically conventional methods depending on their dosage forms. In case of the use of the compound of the present invention in combination with the drugs other than SGLT2 inhibitors, they can be prepared by formulating each active ingredient together or individually.

When the pharmaceutical compositions of the present invention are employed in the practical treatment, the dosage of a compound represented by the above general formula (I), a pharmaceutically acceptable salt thereof or a prodrug thereof as the active ingredient is appropriately decided depending on the age, sex, body weight and degree of symptoms and treatment of each patient, which is approximately within the range of from 0.1 to 1,000 mg per day per adult human in the case of oral administration and approximately within the range of from 0.01 to 300 mg per day per adult human in the case of parenteral administration, and the daily dose can be divided into one to several doses per day and administered suitably. Also, in case of the use of the compound of the present invention in combination with the drugs other than SGLT2 inhibitors, the dosage of the compound of the present invention can be decreased depending on the dosage of the drugs other than SGLT2 inhibitors.

EXAMPLES

The present invention is further illustrated in more detail by way of the following Reference Examples, Examples and Test Examples. However, the present invention is not limited thereto.

Reference Example 1

Dithiocarbonic acid=O-benzyl ester=S-methyl ester

To a suspension of sodium hydride (60%, 8.9 g) in tetrahydrofuran (200 mL) was added benzyl alcohol (20 g) at 0° C., and the mixture was stirred for 30 minutes. To the reaction mixture was added carbon disulfide (42 g), and the mixture was stirred for 1 hour. To the reaction mixture was added methyl iodide (92 g), and the mixture was stirred at room temperature for 3 hours. The reaction mixture was poured into water, and the mixture was extracted with diethyl ether. The organic layer was washed with brine and water, and dried over anhydrous magnesium sulfate. The solvent was removed under reduced pressure, and the residue was purified by column chromatography on silica gel (eluent: hexane/dichloromethane=10/1) to give the title compound (36 g).

Reference Example 2

3-Oxothiobutyric acid=O-benzyl ester

A mixture of dithiocarbonic acid=O-benzyl ester=S-methyl ester (29 g) and acetone (8.5 g) was dropwise added to a suspension of sodium amide (11 g) in toluene (150 mL) at 0° C. over 1 hour, and the mixture was stirred for additional 1 hour. The reaction mixture was poured into 1 mol/L hydrochloric acid solution, and the mixture was extracted with diethyl ether. The organic layer was washed with brine and dried over anhydrous magnesium sulfate, and the solvent was removed under reduced pressure. The residue was purified by column chromatography on silica gel (eluent: hexane/dichloromethane=1/1) to give the title compound (12 g).

Reference Example 3

3-Benzyloxy-5-methyl-1-phenyl-1H-pyrazole

To a solution of 3-oxothiobutyric acid=O-benzyl ester (10 g) and triethylamine (13 mL) in acetonitrile (100 mL) was added phenylhydrazine (4.7 mL), and the mixture was stirred at room temperature overnight. The reaction mixture was poured into water, and the mixture was extracted with diethyl ether. The organic layer was washed with brine and dried over anhydrous magnesium sulfate, and the solvent was removed under reduced pressure. The residue was purified by column chromatography on silica gel (eluent: dichloromethane) to give the title compound (5.2 g).

$^1$H-NMR (CDCl$_3$) δ ppm: 2.29 (3H, d, J=0.7 Hz), 5.26 (2H, s), 5.65-5.75 (1H, m), 7.25-7.55 (10H, m)

Reference Example 4

3-Benzyloxy-1-(4-fluorophenyl)-5-methyl-1H-pyrazole

The title compound was prepared in a similar manner to that described in Reference Example 3 using 4-fluorophenyl-hydrazine hydrochloride instead of phenylhydrazine.

$^1$H-NMR (CDCl$_3$) δ ppm: 2.26 (3H, s), 5.24 (2H, s), 5.69 (1H, s), 7.10-7.20 (2H, m), 7.25-7.50 (7H, m)

Reference Example 5

3-Benzyloxy-4-formyl-5-methyl-1-phenyl-1H-pyrazole

To a solution of 3-benzyloxy-5-methyl-1-phenyl-1H-pyrazole (5.1 g) in N,N-dimethylformamide (30 mL) was added phosphorus oxychloride (2.2 mL) at 80° C., and the mixture was stirred for 1 hour. After cooling to room temperature, the reaction mixture was poured into 1 mol/L aqueous sodium hydroxide solution. The mixture was extracted with diethyl ether, and the organic layer was washed with water and brine and dried over anhydrous magnesium sulfate. The solvent was removed under reduced pressure, and the residue was purified by column chromatography on silica gel (eluent: dichloromethane) to give the title compound (4.6 g).

$^1$H-NMR (CDCl$_3$) δ ppm: 2.55 (3H, s), 5.37 (2H, s), 7.30-7.55 (10H, m), 9.95 (1H, s)

Reference Example 6

3-Benzyloxy-1-(4-fluorophenyl)-4-formyl-5-methyl-1H-pyrazole

The title compound was prepared in a similar manner to that described in Reference Example 5 using 3-benzyloxy-1-(4-fluorophenyl)-5-methyl-1H-pyrazole instead of 3-benzyloxy-5-methyl-1-phenyl-1H-pyrazole.

$^1$H-NMR (CDCl$_3$) δ ppm: 2.53 (3H, s), 5.36 (2H, s), 7.15-7.25 (2H, m), 7.30-7.45 (5H, m), 7.45-7.50 (2H, m), 9.95 (1H, s)

Example 1

4-[(4-Methoxyphenyl)methyl]-5-methyl-1-phenyl-1,2-dihydro-3H-pyrazol-3-one

A Grignard reagent was prepared from 4-bromoanisole (1.2 g), magnesium (0.16 g), a catalytic amount of iodine and tetrahydrofuran (20 mL) in the usual manner. To the obtained Grignard reagent solution was added a solution of 3-benzyloxy-4-formyl-5-methyl-1-phenyl-1H-pyrazole (1.5 g) in tetrahydrofuran (15 mL) at 0° C., and the mixture was stirred for 30 minutes. To the reaction mixture was added a saturated aqueous ammonium chloride solution, and the mixture was extracted with diethyl ether. The organic layer was washed with brine and dried over anhydrous magnesium sulfate, and the solvent was removed under reduced pressure. The residue was dissolved in methanol (50 mL) and tetrahydrofuran (50 mL). To the solution was added 10% palladium-carbon powder, and the mixture was stirred at room temperature under a hydrogen atmosphere overnight. Insoluble materials were removed by filtration, and the solvent of the filtrate was removed under reduced pressure. To the residue was added ethanol, and the precipitates was collected by filtration, washed with ethanol and hexane, and dried under reduced pressure to give the title compound (0.78 g).

$^1$H-NMR (CDCl$_3$) δ ppm: 2.15 (3H, s), 3.66 (2H, s), 3.77 (3H, s), 6.75-6.85 (2H, m), 7.10-7.25 (2H, m), 7.25-7.50 (5H, m)

Example 2

4-[(4-Ethylphenyl)methyl]-5-methyl-1-phenyl-1,2-dihydro-3H-pyrazol-3-one

The title compound was prepared in a similar manner to that described in Example 1 using 1-bromo-4-ethylbenzene instead of 4-bromoanisole.

$^1$H-NMR (CDCl$_3$) δ ppm: 1.21 (3H, t, J=7.6 Hz), 2.16 (3H, s), 2.60 (2H, q, J=7.6 Hz), 3.69 (2H, s), 7.05-7.15 (2H, m), 7.15-7.25 (2H, m), 7.25-7.45 (5H, m)

Example 3

4-[(4-Ethoxyphenyl)methyl]-5-methyl-1-phenyl-1,2-dihydro-3H-pyrazol-3-one

The title compound was prepared in a similar manner to that described in Example 1 using 1-bromo-4-ethoxybenzene instead of 4-bromoanisole.

$^1$H-NMR (CDCl$_3$) δ ppm: 1.38 (3H, t, J=7.0 Hz), 2.14 (3H, s), 3.65 (2H, s), 3.99 (2H, q, J=7.0 Hz), 6.75-6.85 (2H, m), 7.10-7.20 (2H, m), 7.25-7.50 (5H, m)

Example 4

4-[(4-Isopropoxyphenyl)methyl]-5-methyl-1-phenyl-1,2-dihydro-3H-pyrazol-3-one The title compound was prepared in a similar manner to that described in Example 1 using 1-bromo-4-isopropoxybenzene instead of 4-bromoanisole.

$^1$H-NMR (CDCl$_3$) δ ppm: 1.31 (6H, d, J=6.0 Hz), 2.15 (3H, s), 3.65 (2H, s), 4.40-4.55 (1H, m), 6.70-6.85 (2H, m), 7.10-7.20 (2H, m), 7.25-7.50 (5H, m)

Example 5

5-Methyl-4-[(4-methylphenyl)methyl]-1-phenyl-1,2-dihydro-3H-pyrazol-3-one

The title compound was prepared in a similar manner to that described in Example 1 using 4-bromotoluene instead of 4-bromoanisole.

$^1$H-NMR (CDCl$_3$) δ ppm: 2.14 (3H, s), 2.30 (3H, s), 3.68 (2H, s), 7.00-7.10 (2H, m), 7.10-7.20 (2H, m), 7.25-7.50 (5H, m)

Example 6

4-{[4-(2-Hydroxyethyl)phenyl]methyl}-5-methyl-1-phenyl-1,2-dihydro-3H-pyrazol-3-one To a solution of 4-bromophenethyl alcohol (0.21 g) in tetrahydrofuran (20 mL) was added tert-butyllithium (1.6 mol/L pentane solution, 1.5 mL) at −78° C. under an argon atmosphere, and the mixture was stirred for 30 minutes. To the reaction mixture was added a solution of 3-benzyloxy-4-formyl-5-methyl-1-phenyl-1H-pyrazole (0.10 g) in tetrahydrofuran (3 mL), and the mixture was warmed to 0° C. and stirred for 30 minutes. The reaction mixture was poured into a saturated aqueous ammonium chloride solution, and the mixture was extracted with diethyl ether. The organic layer was washed with water and dried over anhydrous magnesium sulfate, and the solvent was removed under reduced pressure. The residue was purified by column chromatography on silica gel (eluent: hexane/ethyl acetate=1/1-1/2) to give an oily substance. The obtained oily substance was dissolved in methanol (4 mL). To the solution was added 10% palladium-carbon powder (0.044 g), and the mixture was stirred at room temperature under a hydrogen atmosphere for 17 hours. Insoluble materials were removed by filtration, and the solvent of the filtrate was removed under reduced pressure. Diethyl ether was added to the residue, and the resulting precipitates were collected by filtration and dried under reduced pressure to give the title compound (0.032 g).

$^1$H-NMR (DMSO-d$_6$) δ ppm: 2.21 (3H, s), 2.66 (2H, t, J=7.1 Hz), 3.55 (2H, t, J=7.1 Hz), 3.60 (2H, s), 4.58 (1H, brs), 7.00-7.20 (4H, m), 7.20-7.35 (1H, m), 7.35-7.50 (4H, m), 9.98 (1H, brs)

Example 7

4-[(4-Ethylphenyl)methyl]-1-(4-fluorophenyl)-5-methyl-1,2-dihydro-3H-pyrazol-3-one The title compound was prepared in a similar manner to that described in Example 1 using 1-bromo-4-ethylbenzene and 3-benzyloxy-1-(4-fluorophenyl)-4-formyl-5-methyl-1H-pyrazole instead of 4-bromoanisole and 3-benzyloxy-4-formyl-5-methyl-1-phenyl-1H-pyrazole, respectively.

$^1$H-NMR (CDCl$_3$) δ ppm: 1.21 (3H, t, J=7.7 Hz), 2.13 (3H, s), 2.61 (2H, q, J=7.7 Hz), 3.68 (2H, s), 7.05-7.20 (6H, m), 7.25-7.40 (2H, m)

Example 8

5-Methyl-4-[(4-methylthiophenyl)methyl]-1-phenyl-1,2-dihydro-3H-pyrazol-3-one

To a solution of 1-bromo-4-methylthiobenzene (0.21 g) in tetrahydrofuran (10 mL) was added tert-butyllithium (1.6 mol/L pentane solution, 0.67 mL) at −78° C. under an argon atmosphere, and the mixture was stirred for 5 minutes. To the reaction mixture was added a solution of 3-benzyloxy-4-formyl-5-methyl-1-phenyl-1H-pyrazole (0.20 g) in tetrahydrofuran (3 mL), and the mixture was warmed to 0° C. and stirred for 30 minutes. The reaction mixture was poured into a saturated aqueous ammonium chloride solution, and the mixture was extracted with diethyl ether. The organic layer was washed with water and dried over anhydrous magnesium sulfate, and the solvent was removed under reduced pressure. To the residue was added hexane, and the precipitates were collected by filtration to give a white crystals. The obtained crystals were dissolved in methanol (5 mL) and tetrahydrofuran (6 mL). To a solution was added 10% palladium-carbon powder (0.30 g), and the mixture was stirred at room temperature under a hydrogen atmosphere for 16 hours. Insoluble materials were removed by filtration, and the solvent of the filtrate were removed under reduced pressure. The residue was purified by column chromatography on silica gel (eluent: hexane/ethyl acetate=6/1-3/1) to give an oily substance. The obtained oily substance was dissolved in trifluoroacetic acid (1.9 mL) and water (0.1 mL), and to the solution was added dimethyl sulfide (0.2 mL), and the mixture was stirred at room temperature for 3 hours. The reaction mixture was concentrated under reduced pressure, and the residue was purified by column chromatography on silica gel (eluent: hexane/ethyl acetate=2/1) to give the title compound (0.054 g).

$^1$H-NMR (CDCl$_3$) δ ppm: 2.19 (3H, s), 2.47 (3H, s), 3.73 (2H, s), 7.15-7.25 (4H, m), 7.25-7.40 (2H, m), 7.45-7.60 (3H, m)

Example 9

4-[(4-Methoxyphenyl)methyl]-5-methyl-1-phenyl-3-(2,3,4,6-tetra-O-acetyl-β-D-glucopyranosyloxy)-1H-pyrazole To a solution of 4-[(4-methoxyphenyl)methyl]-5-methyl-1-phenyl-1,2-dihydro-3H-pyrazol-3-one (0.50 g), aceto-bromo-β-D-glucose (0.84 g) and benzyltri(n-butyl)ammonium chloride (0.53 g) in dichloromethane (16 mL) was added an aqueous sodium hydroxide solution (2 mol/L, 4.3 mL), and the mixture was stirred at room temperature for 1 hour. The reaction mixture was purified by column chromatography on aminopropyl silica gel (eluent: dichloromethane), and successively by column chromatography on silica gel (eluent: hexane/ethyl acetate=1/1) to give the title compound (0.38 g).

$^1$H-NMR (CDCl$_3$) δ ppm: 1.92 (3H, s), 2.01 (3H, s), 2.03 (3H, s), 2.03 (3H, s), 2.18 (3H, s), 3.59 (1H, d, J=15.6 Hz), 3.67 (1H, d, J=15.6 Hz), 3.77 (3H, s), 3.80-3.95 (1H, m), 4.15 (1H, dd, J=2.2, 12.4 Hz), 4.26 (1H, dd, J=4.9, 12.4 Hz), 5.15-5.35 (3H, m), 5.65-5.75 (1H, m), 6.75-6.85 (2H, m), 7.05-7.15 (2H, m), 7.25-7.50 (5H, m)

Example 10

4-[(4-Ethylphenyl)methyl]-5-methyl-1-phenyl-3-(2,3,4,6-tetra-O-acetyl-β-D-glucopyranosyloxy)-1H-pyrazole The title compound was prepared in a similar manner to that described in Example 9 using 4-[(4-ethylphenyl)methyl]-5-methyl-1-phenyl-1,2-dihydro-3H-pyrazol-3-one instead of 4-[(4-methoxyphenyl)methyl]-5-methyl-1-phenyl-1,2-dihydro-3H-pyrazol-3-one.

$^1$H-NMR (CDCl$_3$) δ ppm: 1.20 (3H, t, J=7.6 Hz), 1.90 (3H, s), 2.01 (3H, s), 2.03 (3H, s), 2.03 (3H, s), 2.19 (3H, s), 2.60 (2H, q, J=7.6 Hz), 3.61 (1H, d, J=15.4 Hz), 3.71 (1H, d, J=15.4 Hz), 3.80-3.90 (1H, m), 4.15 (1H, dd, J=2.3, 12.3 Hz), 4.26 (1H, dd, J=4.5, 12.3 Hz), 5.10-5.35 (3H, m), 5.71 (1H, d, J=7.7 Hz), 7.00-7.20 (4H, m), 7.25-7.50 (5H, m)

Example 11

4-[(4-Ethoxyphenyl)methyl]-5-methyl-1-phenyl-3-(2,3,4,6-tetra-O-acetyl-β-D-glucopyranosyloxy)-1H-pyrazole The title compound was prepared in a similar manner to that described in Example 9 using 4-[(4-ethyoxyphenyl)methyl]-5-methyl-1-phenyl-1,2-dihydro-3H-pyrazol-3-one instead of 4-[(4-methoxyphenyl)methyl]-5-methyl-1-phenyl-1,2-dihydro-3H-pyrazol-3-one.

$^1$H-NMR (CDCl$_3$) δ ppm: 1.39 (3H, t, J=6.9 Hz), 1.92 (3H, s), 2.02 (3H, s), 2.03 (3H, s), 2.03 (3H, s), 2.18 (3H, s), 3.58 (1H, d, J=15.8 Hz), 3.67 (1H, d, J=15.8 Hz), 3.80-3.95 (1H, m), 3.99 (2H, q, J=6.9 Hz), 4.15 (1H, dd, J=2.3, 12.4 Hz), 4.27 (1H, dd, J=4.4, 12.4 Hz), 5.10-5.35 (3H, m), 5.72 (1H, d, J=7.7 Hz), 6.75-6.85 (2H, m), 7.05-7.15 (2H, m), 7.25-7.50 (5H, m)

Example 12

4-[(4-Isopropoxyphenyl)methyl]-5-methyl-1-phenyl-3-(2,3,4,6-tetra-O-acetyl-β-D-glucopyranosyloxy)-1H-pyrazole The title compound was prepared in a similar manner to that described in Example 9 using 4-[(4-isopropoxyphenyl)-methyl]-5-methyl-1-phenyl-1,2-dihydro-3H-pyrazol-3-one instead of 4-[(4-methoxyphenyl)methyl]-5-methyl-1-phenyl-1,2-dihydro-3H-pyrazol-3-one.

$^1$H-NMR (CDCl$_3$) δ ppm: 1.30 (3H, d, J=6.1 Hz), 1.31 (3H, d, J=6.1 Hz), 1.91 (3H, s), 2.02 (3H, s), 2.02 (3H, s), 2.03 (3H, s), 2.18 (3H, s), 3.58 (1H, d, J=15.6 Hz), 3.67 (1H, d, J=15.6 Hz), 3.80-3.95 (1H, m), 4.10-4.20 (1H, m), 4.20-

4.35 (1H, m), 4.40-4.55 (1H, m), 5.10-5.35 (3H, m), 5.71 (1H, d, J=7.4 Hz), 6.70-7.85 (2H, m), 7.05-7.15 (2H, m), 7.25-7.50 (5H, m)

Example 13

5-Methyl-4-[(4-methylphenyl)methyl]-1-phenyl-3-(2,3,4,6-tetra-O-acetyl-β-D-glucopyranosyloxy)-1H-pyrazole The title compound was prepared in a similar manner to that described in Example 9 using 5-methyl-4-[(4-methylphenyl)-methyl]-1-phenyl-1,2-dihydro-3H-pyrazol-3-one instead of 4-[(4-methoxyphenyl)methyl]-5-methyl-1-phenyl-1,2-dihydro-3H-pyrazol-3-one.

$^1$H-NMR (CDCl$_3$) δ ppm: 1.91 (3H, s), 2.02 (3H, s), 2.03 (3H, s), 2.03 (3H, s), 2.18 (3H, s), 2.29 (3H, s), 3.60 (1H, d, J=15.3 Hz), 3.70 (1H, d, J=15.3 Hz), 3.80-3.95 (1H, m), 4.15 (1H, dd, J=2.4, 12.4 Hz), 4.26 (1H, dd, J=4.4, 12.4 Hz), 5.10-5.35 (3H, m), 5.72 (1H, d, J=7.5 Hz), 7.00-7.15 (4H, m), 7.25-7.50 (5H, m)

Example 14

4-{[4-(2-Hydroxyethyl)phenyl]methyl}-5-methyl-1-phenyl-3-(2,3,4,6-tetra-O-acetyl-β-D-glucopyranosyloxy)-1H-pyrazole The title compound was prepared in a similar manner to that described in Example 9 using 4-{[4-(2-hydroxyethyl)-phenyl]methyl}-5-methyl-1-phenyl-1,2-dihydro-3H-pyrazol-3-one instead of 4-[(4-methoxyphenyl)methyl]-5-methyl-1-phenyl-1,2-dihydro-3H-pyrazol-3-one.

$^1$H-NMR (CDCl$_3$) δ ppm: 1.91 (3H, s), 2.01 (3H, s), 2.03 (3H, s), 2.03 (3H, s), 2.20 (3H, s), 2.82 (2H, t, J=6.3 Hz), 3.63 (1H, d, J=15.7 Hz), 3.71 (1H, d, J=15.7 Hz), 3.80-3.90 (3H, m), 4.13 (1H, dd, J=2.3, 12.3 Hz), 4.25 (1H, dd, J=4.6, 12.3 Hz), 5.10-5.35 (3H, m), 5.70-5.80 (1H, m), 7.05-7.20 (4H, m), 7.25-7.50 (5H, m)

Example 15

4-[(4-Ethylphenyl)methyl]-1-(4-fluorophenyl)-5-methyl-3-(2, 3,4,6-tetra-O-acetyl-β-D-glucopyranosyloxy)-1H-pyrazole The title compound was prepared in a similar manner to that described in Example 9 using 4-[(4-ethylphenyl)methyl]-1-(4-fluorophenyl)-5-methyl-1,2-dihydro-3H-pyrazol-3-one instead of 4-[(4-methoxyphenyl)methyl]-5-methyl-1-phenyl-1,2-dihydro-3H-pyrazol-3-one.

$^1$H-NMR (CDCl$_3$) δ ppm: 1.20 (3H, t, J=7.6 Hz), 1.90 (3H, s), 2.02 (3H, s), 2.03 (3H, s), 2.04 (3H, s), 2.16 (3H, s), 2.60 (2H, q, J=7.6 Hz), 3.60 (1H, d, J=15.8 Hz), 3.70 (1H, d, J=15.8 Hz), 3.80-3.90 (1H, m), 4.15 (1H, dd, J=2.3, 12.2 Hz), 4.27 (1H, dd, J=4.3, 12.2 Hz), 5.10-5.35 (3H, m), 5.69 (1H, d, J=7.6 Hz), 7.05-7.15 (6H, m), 7.30-7.40 (2H, m)

Example 16

5-Methyl-4-[(4-methylthiophenyl)methyl]-1-phenyl-3-(2,3,4,6-tetra-O-acetyl-β-D-glucopyranosyloxy)-1H-pyrazole The title compound was prepared in a similar manner to that described in Example 9 using 5-methyl-4-[(4-methylthiophenyl)methyl]-1-phenyl-1,2-dihydro-3H-pyrazol-3-one instead of 4-[(4-methoxyphenyl)methyl]-5-methyl-1-phenyl-1,2-dihydro-3H-pyrazol-3-one.

$^1$H-NMR (CDCl$_3$) δ ppm: 1.91 (3H, s), 2.02 (3H, s), 2.03 (3H, s), 2.04 (3H, s), 2.18 (3H, s), 2.45 (3H, s), 3.61 (1H, d, J=15.8 Hz), 3.69 (1H, d, J=15.8 Hz), 3.85-3.95 (1H, m), 4.10-4.40 (2H, m), 5.10-5.35 (3H, m), 5.65-5.75 (1H, m), 7.10-7.20 (4H, m), 7.25-7.50 (5H, m)

Example 17

3-(β-D-Glucopyranosyloxy)-4-[(4-methoxyphenyl)methyl]-5-methyl-1-phenyl-1H-pyrazole To a solution of 4-[(4-methoxyphenyl)methyl]-5-methyl-1-phenyl-3-(2,3,4,6-tetra-O-acetyl-β-D-glucopyranosyloxy)-1H-pyrazole(0.38 g) in methanol (5 mL) was added sodium methoxide (28% methanol solution, 0.12 mL), and the mixture was stirred at room temperature for 1 hour. The reaction mixture was concentrated under reduced pressure, and the residue was purified by column chromatography on silica gel (eluent: dichloromethane/methanol=10/1) to give the title compound (0.32 g).

$^1$H-NMR (CD$_3$OD) δ ppm: 2.12 (3H, s), 3.30-3.50 (4H, m), 3.60-3.90 (7H, m), 5.20-5.30 (1H, m), 6.75-6.85 (2H, m), 7.15-7.25 (2H, m), 7.35-7.55 (5H, m)

Example 18

4-[(4-Ethylphenyl)methyl]-3-(β-D-glucopyranosyloxy)-5-methyl-1-phenyl-1H-pyrazole The title compound was prepared in a similar manner to that described in Example 17 using 4-[(4-ethylphenyl)methyl]-5-methyl-1-phenyl-3-(2,3,4,6-tetra-O-acetyl-β-D-glucopyranosyloxy)-1H-pyrazole instead of 4-[(4-methoxyphenyl)-methyl]-5-methyl-1-phenyl-3-(2,3,4,6-tetra-O-acetyl-β-D-glucopyranosyloxy)-1H-pyrazole.

$^1$H-NMR (CD$_3$OD) δ ppm: 1.19 (3H, t, J=7.6 Hz), 2.12 (3H, s), 2.58 (2H, q, J=7.6 Hz), 3.30-3.50 (4H, m), 3.60-3.70 (1H, m), 3.70-3.90 (3H, m), 5.20-5.30 (1H, m), 7.05-7.20 (4H, m), 7.35-7.55 (5H, m)

Example 19

4-[(4-Ethoxyphenyl)methyl]-3-(β-D-glucopyranosyloxy)-5-methyl-1-phenyl-1H-pyrazole The title compound was prepared in a similar manner to that described in Example 17 using 4-[(4-ethyoxyphenyl)methyl]-5-methyl-1-phenyl-3-(2,3,4,6-tetra-O-acetyl-β-D-glucopyranosyloxy)-1H-pyrazole instead of 4-[(4-methoxyphenyl)-methyl]-5-methyl-1-phenyl-3-(2,3,4,6-tetra-O-acetyl-β-D-glucopyranosyloxy)-1H-pyrazole.

$^1$H-NMR (CD$_3$OD) δ ppm: 1.35 (3H, t, J=7.0 Hz), 2.12 (3H, s), 3.30-3.50 (4H, m), 3.66 (1H, dd, J=5.0, 12.0 Hz), 3.70 (1H, d, J=15.7 Hz), 3.77 (1H, d, J=15.7 Hz), 3.83 (1H, dd, J=1.4, 12.0 Hz), 3.98 (2H, q, J=7.0 Hz), 5.20-5.30 (1H, m), 6.75-6.85 (2H, m), 7.10-7.20 (2H, m), 7.30-7.55 (5H, m)

Example 20

3-(β-D-Glucopyranosyloxy)-4-[(4-isopropoxyphenyl)methyl]-5-methyl-1-phenyl-1H-pyrazole The title compound was prepared in a similar manner to that described in Example 17 using 4-[(4-isopropoxyphenyl)-methyl]-5-methyl-1-phenyl-3-(2,3,4,6-tetra-O-acetyl- β-D-glucopyranosyloxy)-1H-pyrazole instead of 4-[(4-methoxyphenyl)methyl]-5-methyl-1-phenyl-3-(2,3,4,6-tetra-O-acetyl-β-D-glucopyranosyloxy)-1H-pyrazole.

$^1$H-NMR (CD$_3$OD) δ ppm: 1.20-1.30 (6H, m), 2.13 (3H, s), 3.30-3.50 (4H, m), 3.60-3.90 (4H, m), 4.45-4.60 (1H, m), 5.20-5.30 (1H, m), 6.75-6.85 (2H, m), 7.10-7.20 (2H, m), 7.35-7.55 (5H, m)

Example 21

3-(β-D-Glucopyranosyloxy)-5-methyl-4-[(4-methylphenyl)-methyl]-1-phenyl-1H-pyrazole The title compound was prepared in a similar manner to that described in Example 17 using 5-methyl-4-[(4-methylphenyl)methyl]-1-phenyl-3-(2,3,4,6-tetra-O-acetyl-β-D-glucopyranosyloxy)-1H-pyrazole instead of 4-[(4-methoxyphenyl)methyl]-5-methyl-1-phenyl-3-(2,3,4,6-tetra-O-acetyl-β-D-glucopyranosyloxy)-1H-pyrazole.

$^1$H-NMR (CD$_3$OD) δ ppm: 2.11 (3H, s), 2.27 (3H, s), 3.30-3.50 (4H, m), 3.60-3.90 (4H, m), 5.20-5.30 (1H, m), 7.00-7.10 (2H, m), 7.10-7.20 (2H, m), 7.30-7.55 (5H, m)

Example 22

3-(β-D-Glucopyranosyloxy)-4-{[4-(2-hydroxyethyl)phenyl]-methyl}-5-methyl-1-phenyl-1H-pyrazole The title compound was prepared in a similar manner to that described in Example 17 using 4-{[4-(2-hydroxyethyl)-phenyl]methyl}-5-methyl-1-phenyl-3-(2,3,4,6-tetra-O-acetyl-β-D-glucopyranosyloxy)-1H-pyrazole instead of 4-[(4-methoxyphenyl)methyl]-5-methyl-1-phenyl-3-(2,3,4,6-tetra-O-acetyl-β-D-glucopyranosyloxy)-1H-pyrazole.

$^1$H-NMR (CD$_3$OD) δ ppm: 2.12 (3H, s), 2.77 (2H, t, J=7.1 Hz), 3.30-3.50 (4H, m), 3.60-3.90 (6H, m), 5.20-5.30 (1H, m), 7.10-7.15 (2H, m), 7.15-7.25 (2H, m), 7.35-7.55 (5H, m)

Example 23

4-[(4-Ethylphenyl)methyl]-1-(4-fluorophenyl)-3-(β-D-glucopyranosyloxy)-5-methyl-1H-pyrazole The title compound was prepared in a similar manner to that described in Example 17 using 4-[(4-ethylphenyl)methyl]-1-(4-fluorophenyl)-5-methyl-3-(2,3,4,6-tetra-O-acetyl-β-D-glucopyranosyloxy)-1H-pyrazole instead of 4-[(4-methoxyphenyl)methyl]-5-methyl-1-phenyl-3-(2,3,4,6-tetra-O-acetyl-β-D-glucopyranosyloxy)-1H-pyrazole.

$^1$H-NMR (CD$_3$OD) δ ppm: 1.19 (3H, t, J=7.6 Hz), 2.10 (3H, s), 2.58 (2H, q, J=7.6 Hz), 3.30-3.50 (4H, m), 3.60-3.90 (4H, m), 5.20-5.30 (1H, m), 7.05-7.25 (6H, m), 7.40-7.50 (2H, m)

Example 24

3-(β-D-Glucopyranosyloxy)-5-methyl-4-[(4-methylthiophenyl)-methyl]-1-phenyl-1H-pyrazole The title compound was prepared in a similar manner to that described in Example 17 using 5-methyl-4-[(4-methylthiophenyl)methyl]-1-phenyl-3-(2,3,4,6-tetra-O-acetyl-β-D-glucopyranosyloxy)-1H-pyrazole instead of 4-[(4-methoxyphenyl)methyl]-5-methyl-1-phenyl-3-(2,3,4,6-tetra-O-acetyl-β-D-glucopyranosyloxy)-1H-pyrazole.

$^1$H-NMR (CD$_3$OD) δ ppm: 2.12 (3H, s), 2.43 (3H, s), 3.30-3.50 (4H, m), 3.60-3.90 (4H, m), 5.20-5.30 (1H, m), 7.10-7.25 (4H, m), 7.35-7.55 (5H, m)

Example 25

3-(6-O-Ethoxycarbonyl-β-D-glucopyranosyloxy)-4-[(4-methoxyphenyl)methyl]-5-methyl-1-phenyl-1H-pyrazole To a solution of 3-(β-D-glucopyranosyloxy)-4-[(4-methoxyphenyl)methyl]-5-methyl-1-phenyl-1H-pyrazole (0.18 g) and 2,6-dimethylpyridine (0.069 mL) in acetonitrile (5 mL) was added ethyl chloroformate (0.045 mL), and the mixture was stirred at room temperature overnight. To the reaction mixture was added 10% aqueous citric acid solution, and the mixture was extracted with ethyl acetate. The organic layer was washed with brine and dried over anhydrous magnesium sulfate, and the solvent was removed under reduced pressure. The residue was purified by column chromatography on silica gel (eluent: dichloromethane/methanol=15/1) to give the title compound (0.13 g).

$^1$H-NMR (CD$_3$OD) δ ppm: 1.21 (3H, t, J=7.1 Hz), 2.11 (3H, s), 3.30-3.50 (3H, m), 3.50-3.60 (1H, m), 3.69 (1H, d, J=16.4 Hz), 3.74 (3H, s), 3.76 (1H, d, J=16.4 Hz), 4.12 (2H, q, J=7.1 Hz), 4.27 (1H, dd, J=5.7, 11.6 Hz), 4.41 (1H, dd, J=2.1, 11.6 Hz), 5.25-5.35 (1H, m), 6.75-6.85 (2H, m), 7.10-7.25 (2H, m), 7.30-7.55 (5H, m)

Example 26

3-(6-O-Ethoxycarbonyl-β-D-glucopyranosyloxy)-4-[(4-ethylphenyl)methyl]-5-methyl-1-phenyl-1H-pyrazole The title compound was prepared in a similar manner to that described in Example 25 using 4-[(4-ethylphenyl)methyl]-3-(β-D-glucopyranosyloxy)-5-methyl-1-phenyl-1H-pyrazole instead of 3-(β-D-glucopyranosyloxy)-4-[(4-methoxyphenyl)-methyl]-5-methyl-1-phenyl-1H-pyrazole.

$^1$H-NMR (CD$_3$OD) δ ppm: 1.15-1.25 (6H, m), 2.11 (3H, s), 2.58 (2H, q, J=7.5 Hz), 3.30-3.50 (3H, m), 3.50-3.60 (1H, m), 3.72 (1H, d, J=16.0 Hz), 3.78 (1H, d, J=16.0 Hz), 4.12 (2H, q, J=7.2 Hz), 4.26 (1H, dd, J=5.2, 11.6 Hz), 4.40 (1H, dd, J=1.7, 11.6 Hz), 5.25-5.35 (1H, m), 7.05-7.20 (4H, m), 7.30-7.55 (5H, m)

Test Example 1

Assay for Inhibitory Effect on Human SGLT2 Activity

1) Construction of the Plasmid Vector Expressing Human SGLT2

Preparation of the cDNA library for PCR amplification was performed by reverse transcription of a total RNA deprived from human kidney (Ori gene) with oligo dT as the primer, using SUPERSCRIPT Preamplification System (Gibco-BRL: LIFE TECHNOLOGIES). The DNA fragment coding for human SGLT2 was amplified by the PCR reaction, in which the human kidney cDNA library described above was used as the template and the following oligo nucleotides 0702F and 0712R, presented as Sequence Numbers 1 and 2 respectively, were used as the primers. The amplified DNA fragment was ligated into pCR-Blunt (Invitrogen), a vector for cloning, according to standard method of the kit. The *Escherichia coli* HB101 was transformed according to usual method and then selection of the transformants was performed on the LB agar medium containing 50 µg/mL of kanamycin. After plasmid DNA was extracted and purified from the one of the transformants, amplifying of the DNA fragment coding for human SGLT2 was performed by the PCR reaction, in which the following oligo nucleotides 0714F and 0715R, presented as Sequence Numbers 3 and 4 respectively, were used as the primers. The amplified DNA fragment was digested with restriction enzymes, Xho I and Hind III, and then purified with Wizard Purification System (Promega). This purified DNA fragment was inserted at the corresponding restriction sites of pcDNA3.1 (−) Myc/His—B (Invitrogen), a vector for expressing of fusion protein. The Escherichia coli HB101 was transformed according to usual method and then selection of the transformant was performed on the LB agar medium containing 100 µg/mL of ampicillin. After plasmid DNA was extracted and purified from this transformant, the base sequence of the DNA fragment inserted at the multicloning sites of the vector pcDNA3. 1 (−) Myc/His—B was analyzed. This clone had a single base substitution (ATC which codes for the isoleucine-433 was substituted by GTC) compared with the human SGLT2 reported by Wells et al (Am. J. Physiol., Vol. 263, pp. 459-465 (1992)). Sequentially, a clone in which valine is substituted for isoleucine-433 was obtained. This plasmid vector expressing human SGLT2 in which the peptide presented as Sequence Number 5 is fused to the carboxyl terminal alanine residue was designated KL29.

```
Sequence Number 1    ATGGAGGAGCACACAGAGGC

Sequence Number 2    GGCATAGAAGCCCCAGAGGA

Sequence Number 3    AACCTCGAGATGGAGGAGCACACAGAGGC

Sequence Number 4    AACAAGCTTGGCATAGAAGCCCCAGAGGA

Sequence Number 5    KLGPEQKLISEEDLNSAVDHHHHHH
```

2) Preparation of the Cells Expressing Transiently Human SGLT2

KL29, the plasmid coding human SGLT2, was transfected into COS-7 cells (RIKEN CELL BANK RCB0539) by electroporation. Electroporation was performed with EC100 Electroporater (E-C APPARATUS CORPORATION) under the condition: 400 V, 1260 µF, $3.2 \times 10^6$ cells of COS-7 cell and 20 µg of KL29 in 800 µL of OPTI-MEM I medium (Gibco-BRL: LIFE TECHNOLOGIES) in the 0.4 cm type cuvette. After the gene transfer, the cells were harvested by centrifugation and resuspended with OPTI-MEM I medium (3.2 mL/cuvette). To each well in 96-wells plate, 125 µL of this cell suspension was added. After overnight culture at 37° C. under 5% $CO_2$, 125 µL of DMEM medium which is containing 10% of fetal bovine serum (Sanko Jyunyaku), 100 units/mL sodium penicillin G (Gibco-BRL: LIFE TECHNOLOGIES), and 100 µg/mL streptomycin sulfate (Gibco-BRL: LIFE TECHNOLOGIES) was added to each well. These cells were cultured until the next day and then they were used for the measurement of the inhibitory activity against the uptake of methyl-α-D-glucopyranoside.

3) Measurement of the Inhibitory Activity Against the Uptake of methyl-α-D-glucopyranoside After a test compound was dissolved in dimethyl sulfoxide and diluted with the uptake buffer (a pH 7.4 buffer containing 140 mM sodium chloride, 2 mM potassium chloride, 1 mM calcium chloride, 1 mM magnesium chloride, 5 mM methyl-α-D-glucopyranoside, 10 mM 2-[4-(2-hydroxyethyl)-1-piperazinyl]ethane sulfonic acid and 5 mM tris (hydroxymethyl) aminomethane), each diluent was used as test sample for measurement of the inhibitory activity.

After removal of the medium of the COS-7 cells expressing transiently human SGLT2, to each well 180 µL of the pretreatment buffer (a pH 7.4 buffer containing 140 mM choline chloride, 2 mM potassium chloride, 1 mM calcium chloride, 1 mM magnesium chloride, 10 mM 2-[4-(2-hydroxyethyl)-1-piperazinyl]ethane sulfonic acid and 5 mM tris (hydroxymethyl)-aminomethane) was added, and the cells were incubated at 37° C. for 10 minutes. After the pretreatment buffer was removed, 200 µL of the same buffer was added again, and the cells were incubated at 37° C. for 10 minutes. The buffer for measurement was prepared by adding and mixing 7 µL of methyl-α-D-(U-14C)glucopyranoside (Amersham Pharmacia Biotech) to 525 µL of the prepared test sample. For the control, the buffer for measurement without any test compound was prepared. For estimate of the basal uptake in the absence of a test compound and sodium, the buffer for measurement of the basal uptake, which contains 140 mM choline chloride in place of sodium chloride, was prepared similarly. After the pretreatment buffer was removed, 75 µL of the each buffer for measurement was added to each well, and the cells were incubated at 37° C. for 2 hours. After the buffer for measurement was removed, 180 µL of the washing buffer (a pH 7.4 buffer containing 140 mM choline chloride, 2 mM potassium chloride, 1 mM calcium chloride, 1 mM magnesium chloride, 10 mM methyl-α-D-glucopyranoside, 10 mM 2-[4-(2-hydroxyethyl)-1-piperazinyl]ethane sulfonic acid and 5 mM tris(hydroxymethyl)aminomethane) was added to each well and immediately removed. After two additional washing, the cells were solubilized by addition of 75 µL of 0.2 mol/L sodium hydroxide to each well. After the cell lysates were transferred to the PicoPlate (Packard) and 150 µL of MicroScint-40 (Packard) was added to each well, the radioactivity was measured with microplate scintillation counter Top count (Packard). The difference in uptake was obtained as 100% value by subtracting the radioactivity in the basal uptake from that in control and then the concentrations at which 50% of uptake were inhibited ($IC_{50}$) were calculated from the concentration-inhibition curve by least square method. The results are shown in the following Table 1.

TABLE 1

| Test compound | $IC_{50}$ value (nM) |
|---|---|
| Example 18 | 270 |
| Example 20 | 200 |
| WAY-123783 | >100000 |

INDUSTRIAL APPLICABILITY

The glucopyranosyloxyboyrazole derivatives represented by the above general formula (I) of the present invention, pharmaceutically acceptable salts thereof and prodrugs thereof show an excellent hypoglycemic effect by excreting excess glucose into the urine through preventing the reabsorption of glucose at the kidney because they exhibit an excellent inhibitory activity in human SGLT2. The present invention can provide drugs for the prevention or treatment of a disease associated with hyperglycemia such as diabetes, diabetic complications, obesity or the like. In addition, since compounds represented by the above general formula (III) or (IV) and salts thereof are important as intermediates in the production of the compounds represented by the above general formula (I), pharmaceutically acceptable salts thereof and prodrugs thereof, the compounds represented by the above general formula (I), pharmaceutically acceptable salts thereof and prodrugs thereof of the present invention can be readily prepared via such compounds.

| [SEQUENCE LISTING FREE TEXT] | |
|---|---|
| Sequence Number 1: | Synthetic DNA primer |
| Sequence Number 2: | Synthetic DNA primer |
| Sequence Number 3: | Synthetic DNA primer |
| Sequence Number 4: | Synthetic DNA primer |
| Sequence Number 5: | Peptide fused to the carboxyl terminal alanine residue of human SGLT2 |

The invention claimed is:

1. A glucopyranosyloxypyrazole derivative represented by the general formula:

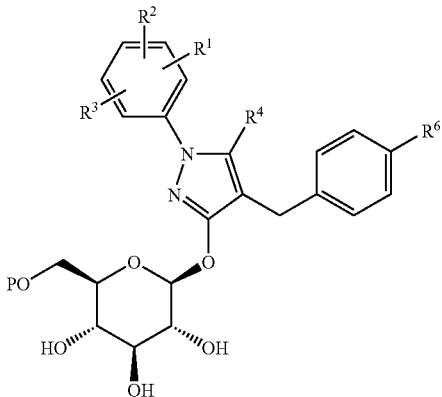

wherein P represents a hydrogen atom or a lower acyl group, a lower alkoxy-substituted (lower acyl) group, a lower alkoxycarbonyl-substituted (lower acyl) group, a lower alkoxycarbonyl group or a lower alkoxy-substituted (lower alkoxycarbonyl) group; $R^1$, $R^2$ and $R^3$ may be the same or different and each represents a hydrogen atom or a halogen atom; $R^4$ represents a lower alkyl group or a halo(lower alkyl) group; and $R^6$ represents a hydrogen atom, a lower alkyl group, a lower alkoxy group, a lower alkylthio group, a halo(lower alkyl) group, a halogen atom, a lower alkenyl group, a cyclic lower alkyl group, a cyclic lower alkoxy group, a cyclic lower alkylidenemethyl group, a 5- or 6-membered aromatic heterocyclic group which contains 1-4 the same or different hetero atoms selected from an oxygen atom, a sulfur atom and a nitrogen atom in the ring, a phenyl group which may have 1-3 the same or different groups selected from a halogen atom and a hydroxy group, or a group represented by the general formula: $P^1$-O-A- wherein $P^1$ represents a hydrogen atom or a lower acyl group, a lower alkoxy-substituted (lower acyl) group, a lower alkoxycarbonyl-substituted (lower acyl) group, a lower alkoxycarbonyl group or a lower alkoxy-substituted (lower alkoxycarbonyl) group; and A represents a lower alkylene group or a pharmaceutically acceptable salt thereof.

2. A glucopyranosyloxypyrazole derivative represented by the general formula:

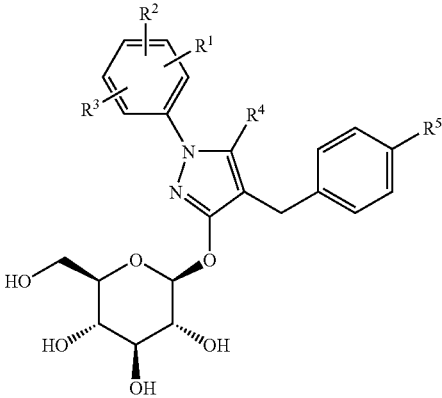

wherein $R^1$, $R^2$ and $R^3$ may be the same or different and each represents a hydrogen atom or a halogen atom; $R^4$ represents a lower alkyl group or a halo(lower alkyl) group; and $R^5$ represents a hydrogen atom, a lower alkyl group, a lower alkoxy group, a lower alkylthio group, a halo(lower alkyl) group, a halogen atom, a lower alkenyl group, a cyclic lower alkyl group, a cyclic lower alkoxy group, a cyclic lower alkylidenemethyl group, a 5- or 6-membered aromatic heterocyclic group which contains 1-4 the same or different hetero atoms selected from an oxygen atom, a sulfur atom and a nitrogen atom in the ring, a phenyl group which may have 1-3 the same or different groups selected from a halogen atom and a hydroxy group, or a group represented by the general formula: HO-A- wherein A represents a lower alkylene group, or a pharmaceutically acceptable salt thereof.

3. A glucopyranosyloxypyrazole derivative as claimed in claim 1 wherein at least one of P and $P^1$ represents a lower acyl group, a lower alkoxy-substituted (lower acyl) group, a lower alkoxycarbonyl-substituted (lower acyl) group, a lower alkoxycarbonyl group or a lower alkoxy-substituted (lower alkoxycarbonyl) group, or a pharmaceutically acceptable salt thereof.

4. A pharmaceutical composition comprising as an active ingredient a glucopyranosyloxypyrazole derivative as claimed in claim 1 or a pharmaceutically acceptable salt thereof in combination with a pharmaceutically acceptable additive.

5. A method for the treatment of a disease associated with hyperglycemia, which comprises administering to a patient in need thereof an effective amount of a glucopyranosyloxypyrazole derivative as claimed in claim 1 or a pharmaceutically acceptable salt thereof.

6. A method as claimed in claim 5 wherein the disease associated with hyperglycemia is diabetes.

7. A method as claimed in claim 5 wherein the disease associated with hyperglycemia is diabetic complications.

8. A method as claimed in claim 5 wherein the disease associated with hyperglycemia is obesity.

9. A method for the manufacture of a pharmaceutical composition for the treatment of a disease associated with hyperglycemia, which method comprises mixing the glucopyranosyloxypyrazole derivative as claimed in claim 1 or a pharmaceutically acceptable salt thereof with a pharmaceutically acceptable additive.

10. A glucopyranosyloxypyrazole derivative represented by the general formula:

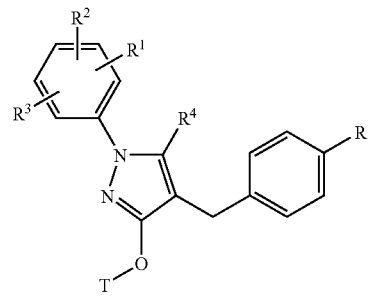

wherein T represents 2,3,4,6-tetra-0-acetyl-β-D-glucopyranosyl group; $R^1$, $R^2$ and $R^3$ may be the same or different and each represents a hydrogen atom or a halogen atom; $R^4$ represents a lower alkyl group or a halo(lower alkyl) group; and R represents a hydrogen atom, a lower alkyl group, a lower alkoxy group, a lower alkylthio group, a halo(lower alkyl) group, a halogen atom, a lower alkenyl group, a cyclic lower alkyl group, a cyclic lower alkoxy group, a cyclic lower alkylidenemethyl group, a 5- or 6-membered aromatic hetero cyclic group which contains 1-4 the same or different hetero atoms selected from an oxygen atom, a sulfur atom and a nitrogen atom in the ring, a phenyl group which may have 1-3 the same or different groups selected from a halogen atom and a hydroxy group, or a group represented by the general formula: $P^{10}$-O-A- wherein $P^{10}$ represents a hydrogen atom or a hydroxy-protective group; and A represents a lower alkylene group, or a salt thereof.

11. The method as in claim 9 wherein the disease associated with hyperglycemia is diabetes.

12. The method as in claim 9 wherein the disease associated with hyperglycemia is diabetic complications.

13. The method as in claim 9 wherein the disease associated with hyperglycemia is obesity.

* * * * *